(12) United States Patent
Hahn et al.

(10) Patent No.: US 8,747,903 B2
(45) Date of Patent: Jun. 10, 2014

(54) COMPOSITION FOR NUCLEIC ACID DELIVERY USING METAL NANOPARTICLES AND PREPARING METHOD THEREOF

(75) Inventors: Sei Kwang Hahn, Pohang (KR); Min-Young Lee, Pohang (KR); Kitae Park, Jeonju (KR); Ki Su Kim, Pohang (KR); Hwiwon Lee, Daegu (KR)

(73) Assignee: Postech Academy-Industry Foundation, Pohang (KR)

( * ) Notice: Subject to any disclaimer, the term of this patent is extended or adjusted under 35 U.S.C. 154(b) by 0 days.

(21) Appl. No.: 13/430,882

(22) Filed: Mar. 27, 2012

(65) Prior Publication Data

US 2013/0095187 A1 Apr. 18, 2013

(30) Foreign Application Priority Data

Oct. 14, 2011 (KR) ........................ 10-2011-0105265

(51) Int. Cl.
| | |
|---|---|
| *A61K 9/14* | (2006.01) |
| *A61K 31/7088* | (2006.01) |
| *A61K 31/713* | (2006.01) |
| *C12N 5/071* | (2010.01) |
| *A61K 31/00* | (2006.01) |
| *B82Y 5/00* | (2011.01) |
| *B82Y 40/00* | (2011.01) |

(52) U.S. Cl.
USPC ........ 424/493; 514/44 R; 514/44 A; 435/375; 427/214; 977/795; 977/890; 977/906

(58) Field of Classification Search
None
See application file for complete search history.

(56) References Cited

U.S. PATENT DOCUMENTS

| | | | |
|---|---|---|---|
| 7,901,711 | B1 | 3/2011 | Sung |
| 2002/0065242 | A1 | 5/2002 | Ford |
| 2008/0138408 | A1 | 6/2008 | Venkatesh |
| 2009/0104114 | A1 | 4/2009 | Tamarkin |

FOREIGN PATENT DOCUMENTS

WO WO-2010-087912 * 8/2010

OTHER PUBLICATIONS

Elbakry A, Layer by Layer assembled gold nanoparticles for siRNA delivery, supporting information, 2009, ACS, NanoLett, 9, 5, 2059-2064.*
Elbakry A, Layer by Layer assembled gold nanoparticles for siRNA delivery, 2009, ACS, NanoLett, 9, 5, 2059-2064.*
Maus, L, Conjugation of peptides to the passivation shell of gold nanoparticles for targeting of cell surface receptors, 2010, ACS, ACSNano, 4, 11, 6617-6628.*
Poon Z, Controlling in vivo stability and biodistribution in electrostatically assembled nanoparticles for systemic delivery, 2011, NanoLett, 11, 2096-2103.*
Poon Z, Supporting Information, NanoLett, 2011, 11, 2096-2103.*
Min-Young Lee et al., "Target-Specific Gene Silencing of Layer-by-Layer Assembled Gold-Cysteamine/siRNA/PEI/HA Nanocomplex", American Chemical Society Nano, Jul. 8, 2011vol. 5, No. 8, pp. 6138-6147.

* cited by examiner

*Primary Examiner* — Frederick Krass
*Assistant Examiner* — Celeste A Roney
(74) *Attorney, Agent, or Firm* — Lexyoume IP Meister, PLLC

(57) ABSTRACT

The present invention relates to a composition for nucleic acid delivery and a method for preparing the same, more particularly to a composition for nucleic acid delivery having excellent stability in the body environment and excellent intracellular delivery efficiency of nucleic acid, and enabling target directed delivery of nucleic acid, and a method for preparing the same.

20 Claims, 18 Drawing Sheets
(17 of 18 Drawing Sheet(s) Filed in Color)

SEQUENCE LISTING

```
<160> NUMBER OF SEQ ID NOS: 12

<210> SEQ ID NO 1
<211> LENGTH: 16
<212> TYPE: RNA
<213> ORGANISM: Artificial Sequence
<220> FEATURE:
<223> OTHER INFORMATION: sense sequence of siLuc with dTdT attached to
      the 3' end

<400> SEQUENCE: 1
uuguuuugga gcgaaa                                                       16

<210> SEQ ID NO 2
<211> LENGTH: 16
<212> TYPE: RNA
<213> ORGANISM: Artificial Sequence
<220> FEATURE:
<223> OTHER INFORMATION: antisense sequence of siLuc with dTdT attached
      to the 3' end

<400> SEQUENCE: 2
uuucgcucca aaacaa                                                       16

<210> SEQ ID NO 3
<211> LENGTH: 21
<212> TYPE: RNA
<213> ORGANISM: Artificial Sequence
<220> FEATURE:
<223> OTHER INFORMATION: sense sequence of siVEGF with TTdTdT attached
      to the 3' end

<400> SEQUENCE: 3
augugaaugc agaccaaaga a                                                 21

<210> SEQ ID NO 4
<211> LENGTH: 21
<212> TYPE: RNA
<213> ORGANISM: Artificial Sequence
<220> FEATURE:
<223> OTHER INFORMATION: antisense sequence of siVEGF with TTdTdT
      attached to the 3' end

<400> SEQUENCE: 4
uucuuugguc ugcauucaca a                                                 21

<210> SEQ ID NO 5
<211> LENGTH: 21
<212> TYPE: RNA
<213> ORGANISM: Artificial Sequence
<220> FEATURE:
<223> OTHER INFORMATION: sense sequence of siApoB with dTdT attached to
```

-continued the 3' end

<400> SEQUENCE: 5
gucaucacac ugaauaccaa u                                              21

<210> SEQ ID NO 6
<211> LENGTH: 21
<212> TYPE: RNA
<213> ORGANISM: Artificial Sequence
<220> FEATURE:
<223> OTHER INFORMATION: antisense sequence of siApoB with dTdT attached
      to the 3' end

<400> SEQUENCE: 6
auugguauuc agugugauga c                                              21

<210> SEQ ID NO 7
<211> LENGTH: 20
<212> TYPE: DNA
<213> ORGANISM: Artificial Sequence
<220> FEATURE:
<223> OTHER INFORMATION: forward Primer of GAPDH

<400> SEQUENCE: 7
aggccggtgc tgagtatgtc                                                20

<210> SEQ ID NO 8
<211> LENGTH: 20
<212> TYPE: DNA
<213> ORGANISM: Artificial Sequence
<220> FEATURE:
<223> OTHER INFORMATION: reverse Primer of GAPDH

<400> SEQUENCE: 8
tgcctgcttc accaccttct                                                20

<210> SEQ ID NO 9
<211> LENGTH: 22
<212> TYPE: DNA
<213> ORGANISM: Artificial Sequence
<220> FEATURE:
<223> OTHER INFORMATION: forward Primer of VEGF

<400> SEQUENCE: 9
ggagatcctt cgaggagcac tt                                             22

<210> SEQ ID NO 10
<211> LENGTH: 25
<212> TYPE: DNA
<213> ORGANISM: Artificial Sequence
<220> FEATURE:
<223> OTHER INFORMATION: reverse Primer of VEGF

<400> SEQUENCE: 10
ggcgatttag cagcagatat aagaa                                          25

<210> SEQ ID NO 11
<211> LENGTH: 21
<212> TYPE: DNA
<213> ORGANISM: Artificial Sequence
<220> FEATURE:
<223> OTHER INFORMATION: forward Primer of ApoB

<400> SEQUENCE: 11
ttttcctccc agatttcaag g                                              21

```
<210> SEQ ID NO 12
<211> LENGTH: 22
<212> TYPE: DNA
<213> ORGANISM: Artificial Sequence
<220> FEATURE:
<223> OTHER INFORMATION: reverse Primer of ApoB

<400> SEQUENCE: 12
tccagcattg gtattcagtg tg                                              22
```

COMPOSITION FOR NUCLEIC ACID DELIVERY USING METAL NANOPARTICLES AND PREPARING METHOD THEREOF

CROSS REFERENCE TO RELATED APPLICATION

This application claims priority to and the benefit of Korean Patent Application No. 10-2011-0105265 filed on Oct. 14, 2011, which is hereby incorporated by reference for all purposes as if fully set forth herein.

BACKGROUND OF THE INVENTION (a) Field of the Invention

The present invention relates to a composition for nucleic acid delivery and a method for preparing the same, more particularly to a composition for nucleic acid delivery, which has excellent stability in the body environment and excellent intracellular nucleic acid delivery efficiency, and is capable of target directed delivery of nucleic acid, and a method for preparing the same.

(b) Description of the Related Art

Recently, industrial importances of small interfering ribonucleic acid (siRNA), antisense oligonucleic acids, plasmid deoxyribonucleic acid, and the like as nucleic acid-based drugs are highlighted. However, to develop nucleic acids as drugs, efficient delivery to cells or tissues should be solved first.

For intracellular delivery of nucleic acids, studies on viral vectors or non-viral vectors using polymer or nanoparticles are under progress. Among them, a viral vector has higher gene delivery efficiency than a non-viral vector, but its application to humans is very limited due to safety problem of using virus. Thus, development of non-viral vectors as a safer alternative to viral vectors is under progress.

Currently, cationic liposome, TAT peptide, or cationic polymer such as polyethylenimine (PEI) is largely used as delivery system for nucleic acid, particularly siRNA. Particularly, it has been reported that cationic polymer of polyethyleneimine (PEI) compresses negatively charged nucleic acids to form colloidal particles, and holds pH buffering capacity even in lysosome in the cells, and thus, delivers plasmid deoxyribonucleic acids to various cells (Boussif et al., Proc. Natl. Acad. Sci. USA 92 (1995) 7297-7301; Godbey et al., J. Controlled Release 60 (1999)149-160).

However, it was found that the cationic polymer causes cell aggregation in the body and binds electrostatically to blood protein to lower siRNA activity, and causes fatal toxicity to body organs such as liver, lung, and the like. Thus, it is known that the cationic polymer is difficult to be utilized alone as siRNA delivery system. And, regarding the use of polyethyleneimine, there are remaining problems relating to intracellular gene delivery efficiency and cytotoxicity, and thus, many studies for solving these problems are under progress. For example, to reduce cytotoxicity of polyethyleneimine (PEI), a method of modification with dextran sulfate, human serum albumin, polyethylene glycol, and the like has been attempted, but the modified PEIs commonly exhibited lower gene delivery efficiency than PEI itself.

Accordingly, there is a need for technology of efficient intracellular delivery of small interfering ribonucleic acid, oligonucleic acid such as antisense oligonucleic acid, and the like, having excellent stability in the body.

Meanwhile, gold nanoparticles are known to have excellent biocompatibility, and the particle size may be controlled and the surface modification is easy, and thus, many studies on binding biomolecules to them are under progress. And, hyaluronic acid is linear polymer polysaccharide consisting of alternating β-D-N-acetylglucosamine and β-D-glucuronic acid, it does not have species- and organ-specificity, and it is known to exhibit excellent biocompatibility even when implanted or injected in the body.

SUMMARY OF THE INVENTION

In order to overcome the problems of the prior art, it is an object of the present invention to provide a composition for nucleic acid delivery having excellent stability in the body environment and excellent intracellular nucleic acid delivery efficiency, and capable of target directed delivery of nucleic acid, a method for preparing the same, and a method for delivering nucleic acid using the composition for nucleic acid delivery.

To achieve the object, as results of studies on technology relating to nucleic acid delivery system having excellent stability in the body and capable of efficiently delivering nucleic acid in the cell, the inventors confirmed that when a polymer self assembled composite that is prepared by sequentially coating nucleic acid, cationic polymer, and anionic polymer on metal nanoparticles by electrostatic layer by layer self assembly so as to protect nucleic acid from the external environment is used as intracellular nucleic acid delivery system, nucleic acid stability in the body and intracellular nucleic acid delivery efficiency may be remarkably improved, and completed the invention.

Therefore, according to one embodiment of the invention, there is provided a composition for nucleic acid delivery comprising positively charged metal nanoparticles; and a nucleic acid layer, a cationic polymer layer and an anionic polymer layer, formed by coating of nucleic acid, cationic polymer and anionic polymer on the surface of the metal nanoparticles by electrostatic layer by layer self assembly.

According to another embodiment of the invention, there is provided a method for preparing a composition for nucleic acid delivery, comprising: reacting metal nanoparticles with positive charge introducing material to introduce positive charge on the surface of the metal nanoparticles; coating nucleic acid on the surface of the positive charge introduced metal nanoparticle surface to form a metal nanoparticle/nucleic acid composite; coating cationic polymer on the metal nanoparticle/nucleic acid composite to form a metal nanoparticle/nucleic acid/cationic polymer composite; and coating anionic polymer on the metal nanoparticle/nucleic acid/cationic polymer composite to form a metal nanoparticle/nucleic acid/cationic polymer/anionic polymer composite, wherein the nucleic acid, cationic polymer, and anionic polymer is coated by electrostatic layer by layer self assembly.

According to yet another embodiment, there is provided a method for delivering nucleic acid using a composition for nucleic acid delivery comprising positively charged metal nanoparticles; and a nucleic acid layer, a cationic polymer layer and an anionic polymer layer, formed by coating of nucleic acid, cationic polymer and anionic polymer on the surface of the metal nanoparticles by electrostatic layer by layer self assembly.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE EMBODIMENTS

Figure 1:
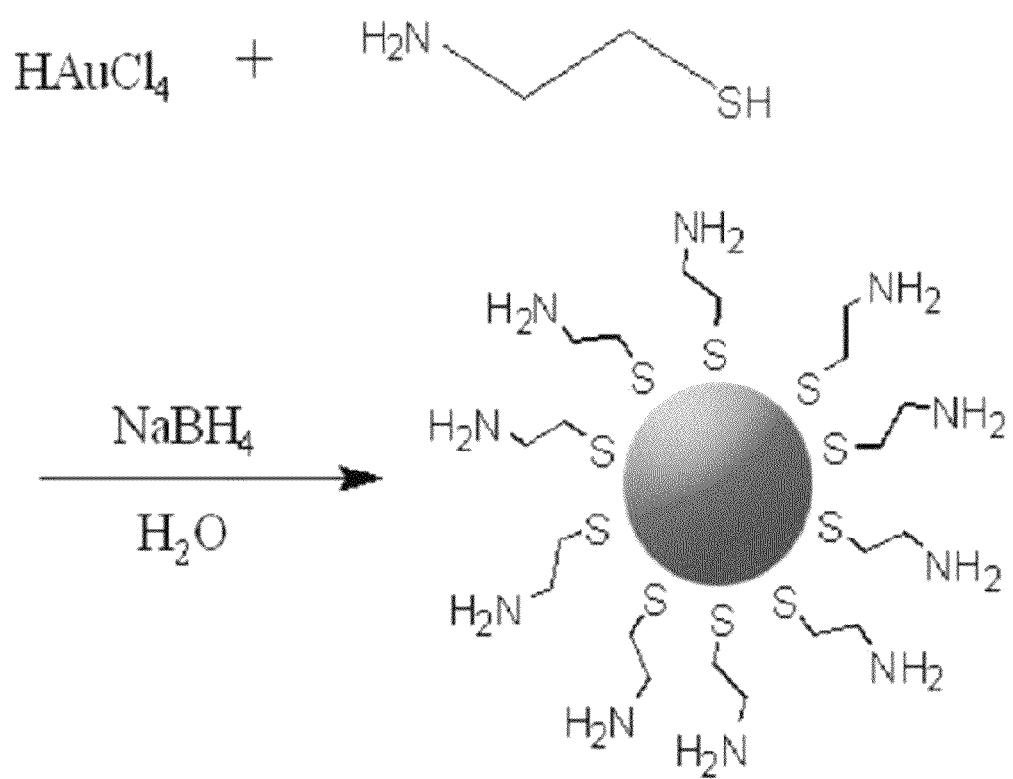
FIG. 1 schematically shows a method of synthesizing positive charge introduced gold nanoparticles (AuCM) by introducing cysteamine on the surface of gold nanoparticles according to <Example 1-1>.

Hereinafter, the present invention will be explained in detail.

One embodiment of the invention provides a composition for nucleic acid delivery comprising positively charged metal nanoparticles; and a nucleic acid layer, a cationic polymer layer and an anionic polymer layer, formed by coating of nucleic acid, cationic polymer and anionic polymer on the surface of the metal nanoparticles by electrostatic layer by layer self assembly.

Another embodiment of the invention provides a method for preparing a composition for nucleic acid delivery, comprising: reacting metal nanoparticles with positive charge introducing material to introduce positive charge on the surface of the metal nanoparticles; coating nucleic acid on the surface of the positive charge introduced metal nanoparticle surface to form a metal nanoparticle/nucleic acid composite; coating cationic polymer on the metal nanoparticle/nucleic acid composite to form a metal nanoparticle/nucleic acid/cationic polymer composite; and coating anionic polymer on the metal nanoparticle/nucleic acid/cationic polymer composite to form a metal nanoparticle/nucleic acid/cationic polymer/anionic polymer composite, wherein the nucleic acid, cationic polymer, and anionic polymer is coated by electrostatic layer by layer self assembly.

As used herein, "electrostatic layer by layer self assembly" refers to a so-called LBL method wherein layers are deposited by electrostatic attraction. The LBL method is a method of alternatively depositing positively charged and negatively charged polymer electrolyte on a charged substrate by electrostatic attraction, and recently, is it also applied to charged nanoparticles (Poon et al., ACS Nano 5 (2011)4284-4292; Kim et al., J. Phys. Chem. C 114 (2010)9917-9922). A method of depositing polymer electrolyte on nanoparticles by electrostatic attraction with the LBL method has advantages of dispensing with a catalyst required at covalent bonding and more rapid and simple preparation. And, if a drug is covalently bonded to nanoparticles, drug activity in the body may be decreased, while if it is deposited by electrostatic attraction according to the LBL method, drug activity in the body is not affected, and thus, drug treatment effect may be further improved.

As used herein, gene silencing refers to decrease in the degree of transcription of target nucleic acid sequence, i.e., targeted genes by RNAi (RNA interference), or decrease in the amount or activity of target sequence or protein.

In the composition for nucleic acid delivery according to one embodiment, layers respectively consisting of nucleic acid, cationic polymer and anionic polymer are sequentially coated on the surface of metal nanoparticles by the above electrostatic layer by layer self assembly, and each layer has opposite charge to the adjacent layer, thus forming a self assembled polymer composite structure having strong bonding by mutual attraction.

More specifically, negatively charged nucleic acid is bound on the positive charge introduced surface of metal nanoparticle microsphere by electrostatic attraction, and self assembly of the nucleic acid-bound metal nanoparticles occurs. Meanwhile, the number of metal nanoparticles that form a self assembled composite may be appropriately controlled by the amount of nucleic acid or material used for surface modification (positive charge introduction) of metal nanoparticle. According to the above explained self assembly of nucleic acid-bound metal nanoparticles, nucleic acid forms a nucleic acid layer that surrounds the metal nanoparticle microsphere self assembled composite, and according to subsequent steps, cationic polymer and anionic polymer are sequentially bound by electrostatic attraction to respectively form a cationic polymer layer and an anionic polymer layer, thus having a microsphere self assembled composite form wherein metal nanoparticle/nucleic acid/cationic polymer/anionic polymer are sequentially coated, thereby effectively protecting nucleic acid bound to the metal nanoparticles from external environment to have remarkably improved stability (see FIG. 3a and FIG. 3b).

As explained above, the composition for nucleic acid delivery may perfectly hide nucleic acid to be delivered in the cell from external environment by sequentially coating nucleic acid, cationic polymer and anionic polymer on the surface of metal nanoparticle, thereby preventing degradation of nucleic acid by nuclease when applied in the body, thus remarkably improving nucleic acid delivery efficiency.

Meanwhile, when nucleic acid is delivered using metal nanoparticle only or using metal nanoparticle and cationic polymer, intracellular nucleic acid delivery efficiency may be decreased as serum concentration increases. However, since the composition for nucleic acid delivery according to one embodiment of the invention has the above-explained structure, it may further increase intracellular nucleic acid delivery efficiency as serum concentration increases, and thus, has excellent serum stability, i.e., stability in the body (see <Experimental Example 3> to <Experimental Example 5>).

In addition, the composition for nucleic acid delivery enable target directed delivery of nucleic acid included in the composition, by coating anionic polymer capable of target directed delivery, preferably hyaluronic acid or a pharmaceutically acceptable salt thereof on the outermost layer (see <Experimental Example 6> to <Experimental Example 9>).

The nanoparticle may be gold nanoparticle, silver nanoparticle, magnetic nanoparticle, silica nanoparticle, or quantum dot, having positive charge introduced on the surface The magnetic nanoparticle may be magnetic metal nanoparticle, and specific examples thereof may include iron oxide (for example, $Fe_2O_3$, $Fe_3O_4$, etc.), Ferrite (for example, $CoFe_2O_4$, $MnFe_2O_4$, etc.), and alloy (for example, alloy with noble metal such as FePt, CoPt, etc. to overcome oxidation due to magnetic atoms, and increase conductivity and stability), but not limited thereto. And, the quantum dot is a particle wherein a nanosized semiconductor particle (CdSe, CdTe, CdS, etc.) forms a core, and it is nanomaterial having a particle size of 10 to 15 nm.

Positive charge may be introduced on the surface of the metal nanoparticle by reacting the metal nanoparticle with positive charge introducing material.

The positive charge introducing material may include any material that may be bound to the nanoparticle surface on one side, and has positive charge on the other side, to which nucleic acid may be bound, without specific limitations. Preferably, the positive charge introducing material can be dopamine, polyethylene glycol (PEG) having introduced thiol group and amine group, cysteine, or cysteamine, more preferably cysteamine.

When cysteamine is used as the positive charge introducing material, metal nanoparticles having positive charge introduced on the surface may be prepared by dissolving metal nanoparticles (for example, $HAuCl_4$) in distilled water together with cysteamine of the following Chemical Formula 1, and adding a reducing agent such as ascorbic acid, lactic acid, sodium citrate or sodium borohydride to react for 6 to 12 hours (see <Example 1-1>).

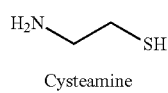

[Chemical Formula 1]

Cysteamine

And, the positive charge introducing material may be preferably used in the mole ratio of 200 to 600:1 (positive charge introducing material: metal nanoparticles) to the metal nanoparticles, but not limited thereto.

The nucleic acid may include any nucleic acid that is to be delivered in the cell without specific limitations, and preferably, it may be selected from the group consisting of deoxyribonucleotide, ribonucleotide, and a polymer thereof having a single stranded or double stranded form, more preferably small interfering ribonucleic acid (siRNA), antisense nucleic acid, or nucleic acid aptamer, still more preferably small interfering ribonucleic acid (siRNA), antisense nucleic acid or nucleic acid aptamer consisting of 5 to 200 base pairs, most preferably small interfering ribonucleic acid (siRNA) consisting of 5 to 200 base pairs.

The step of coating nucleic acid on the positively charged metal nanoparticle surface by electrostatic layer by layer self assembly to form a nucleic acid layer (metal nanoparticle/nucleic acid composite) may include adding a solution including the metal nanoparticles to a solution including the nucleic acid.

About 60% to 80% of the used nucleic acid may be bound to the metal nanoparticles, and preferably the nucleic acid coated on the metal nanoparticle surface and the metal nanoparticle which would be coated with the nucleic acid may be bound in the mole ratio of 40 to 48:1 (nucleic acid: metal nanoparticles), thereby minimizing loss of nucleic acid without precipitation and forming a stable composite including nucleic acid bound in the maximum amount. If exceeding the above range, precipitation may occur, and if fall short of the above range, nucleic acid delivery effect may be insufficient (see <Example 1-2>).

After forming a nucleic acid layer on the positive charge introduced metal nanoparticle surface (metal nanoparticle/nucleic acid composite), a cationic polymer layer may be further formed.

The cationic polymer layer is formed in order to escape endosome formed by intracellular uptake of the composition for nucleic acid delivery and deliver nucleic acid in the cell, and it may be formed by coating cationic polymer on the surface of the nucleic acid layer by electrostatic layer by layer self assembly, and thereby a metal nanoparticle/nucleic acid/cationic polymer composite is formed.

The step of forming the cationic polymer layer (metal nanoparticle/nucleic acid/cationic polymer composite) may include dispersing a solution including the metal nanoparticle/nucleic acid in a solution including cationic polymer.

The cationic polymer may preferably include positively charged polymer capable of escaping from endosome, more preferably poyethyleneimine, chitosan, or polyamidoamine, most preferably polyethyleneimine (PEI) having best endosome escaping performance.

The polyethyleneimine (PEI) is a polymer of ethyleneimine, and it may have molecular weight of 10 kDa to 25 kDa, but not limited thereto.

The amount of cationic polymer bound to nucleic acid in the metal nanoparticle/nucleic acid/cationic polymer composite may be indicated by the ratio of nitrogen to phosphorus (N/P ratio).

The ratio of nitrogen to phosphorus (N/P ratio) means a ratio of nucleic acid charge to single molecule paring, and thus, the N/P charge ratio means the first charge ratio N/P of a single cationic polymer component to single nucleic acid in the first metal nanoparticle/nucleic acid/cationic polymer composite solution.

Preferably, the cationic polymer may be coated at N/P ratio of 1 to 5 to the nucleic acid of the metal nanoparticle/nucleic acid composite. If the ratio exceeds the above range, i.e., the amount of the cationic polymer is too large, toxicity may be exhibited, and if it is fall short of the above range, the cationic polymer, after being uptaken in the cell, may not easily escape from endosome.

After forming the cationic polymer layer, an anionic polymer layer may be further formed.

The anionic polymer layer is formed for target directed delivery of nucleic acid included in the composition for nucleic acid delivery, and it may be formed by coating anionic polymer on the surface of the cationic polymer layer by electrostatic layer by layer self assembly, and thereby, a metal nanoparticle/nucleic acid/cationic polymer/anionic polymer composite may be formed.

The step of forming the anionic polymer layer (metal nanoparticle/nucleic acid/cationic polymer/anionic polymer composite) may include dispersing a solution containing the metal nanoparticle/nucleic acid/cationic polymer in a solution containing anionic polymer.

The anionic polymer may be preferably selected from the group consisting of hyaluronic acid, dextran sulfate, heparin, heparan sulfate, chondroitin, chondroitin sulfate, keratan sulfate, dermatan sulfate, and a pharmaceutically acceptable salt thereof, more preferably hyaluronic acid or a pharmaceutically acceptable salt thereof having very excellent biocompatibility.

The hyaluronic acid (HA) may be natural or synthetic hyaluronic acid, or a salt thereof, and it refers to linear polymer polysaccharides consisting of alternating β-D-N-acetylglucosamine and β-D-glucuronic acid.

The hyaluronic acid or a pharmaceutically acceptable salt thereof may preferably have a molecular weight of 10 kD to 100 kD, but not limited thereto.

And, the mass ratio of the anionic polymer to the cationic polymer of the metal nanoparticle/nucleic acid/cationic polymer composite may be preferably 10 to 30:1, and the charge ratio may be 1 to 3:1. By using the anionic polymer in the above range, the metal nanoparticle/nucleic acid/cationic polymer composite may be perfectly hidden from the external environment, and target directed delivery of nucleic acid may be effectively achieved.

As explained, the composition for nucleic acid delivery according to one embodiment of the invention has the effect of enabling target directed delivery of nucleic acid by including a anionic polymer layer as the outermost layer, and for example, if hyaluronic acid is used as the anionic polymer, target directed delivery to cell or tissue having hyaluronic acid receptor may be achieved.

Accordingly, another embodiment of the invention provide a method of delivering nucleic acid in the cell or tissue using a composition for nucleic acid delivery comprising positively charged metal nanoparticles; and a nucleic acid layer, a cationic polymer layer and an anionic polymer layer formed by coating of nucleic acid, cationic polymer and anionic polymer on the surface of the metal nanoparticles by electrostatic layer by layer self assembly.

The method for delivering nucleic acid may include preparing the composition for nucleic acid delivery; and administering the composition for nucleic acid delivery to a subject in need of the nucleic acid delivery.

The subject may include mammals including human, and cells or tissues thereof.

The composition for nucleic acid delivery may be appropriately formulated according to the use, and it may be administered orally or parentally. For oral administration, it may be used in the form of powder, a granule, a tablet, suspension, emulsion, syrup, and the like. And, for parental administration, it may be administered by intravenous, intramuscular, subcutaneous injection, and the like, but any possible routes of administration may be applied without limitations.

Preferable dosage amount may be those suitable for treatment or prevention of the subject and/or disease, it may be controlled according to various factors including age, gender, general health condition and body weight of the subject, kind and severance of the disease, kind of dosage form, kinds and contents of other ingredients contained in the composition, secretion rate of the composition, administration route and duration, and the like, and it may be appropriately selected by one of ordinary skilled person in the art.

And, preferably, the composition for nucleic acid delivery may further include appropriate carrier, excipient, and diluent, and the like, commonly used in the preparation of a pharmaceutical composition.

The carrier, excipient, and diluents may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and the like.

As explained, the hyaluronic acid enables target directed delivery of nucleic acid and has very excellent biocompatibility, and thus, it may be very usefully applied in the body.

Specifically, according to one experimental example of the invention, as the result of evaluating gene silencing activity of the composition for nucleic acid delivery, it was confirmed that RNA having specific base sequence may be effectively inhibited (see <Experimental Example 5>), and according to another experimental example, as the result of evaluating systemic delivery target directed gene silencing activity of the composition for nucleic acid delivery, it was confirmed that the level of RNA having specific base sequence may be inhibited in a concentration-dependent manner in the liver (see <Experimental Example 8>).

The composition for nucleic acid delivery according to one embodiment of the invention may preferably comprise 90 to 110 parts by weight of the metal nanoparticles, 3.28 to 3.93 parts by weight of the nucleic acid, 3.24 to 3.89 parts by weight of the cationic polymer, and 50.45 to 61.66 parts by weight of the anionic polymer. If exceeding the above range, it may not be preferable because of precipitation, cytotoxicity, and the like, and if fall short of the above range, nucleic acid delivery effect may be insufficient, and delivery to a target may not be properly achieved with effectively protecting nucleic acid from the external environment.

Since the composition for nucleic acid delivery of the present invention may perfectly hide nucleic acid from the external environment, when applied in the body, it may prevent degradation of nucleic acid by nuclease, thus having very excellent intracellular delivery efficiency, and as serum concentration increases, it may further increase intracellular nucleic acid delivery efficiency, thus having very excellent serum stability, i.e., stability in the body.

And, the composition for nucleic acid delivery comprises anionic polymer capable of target directed delivery to the outermost layer, thus enabling target directed delivery of nucleic acid, and since it comprises cationic polymer having excellent endosome escape performance, it may escape from endosome formed by cellular uptake of the composition for nucleic acid delivery and efficiently deliver nucleic acid in the cell.

Hereinafter, the present invention will be explained in detail with reference to the following Examples.

However, these examples are presented only to illustrate the invention, and the scope of the invention is not limited thereto.

<Materials and Source of Acquisition>

Among the materials used in the following Examples, hyaluronic acid (HA) having molecular weight of 100 kDa was purchased from Lifecore Co. (Chaska, Minn.), branched polyethyleneimine (PEI) having molecular weight of 25 kDa, $HAuCl_4$, and $NaBH_4$ were purchased from Sigma-Aldrich (St. Louis, Mo.). And, cysteamine dihydrochloride was purchased from Tokyo Chemical Industry Co. (Tokyo, Japan), and dimethyl sulfoxide (DMSO) was purchased from Junsei Chemical Co. (Tokyo, Japan).

Mouse malignant melanoma B16F1 cell line was purchased from Korean Cell Line Bank (Seoul, Republic of Korea)), DMEM, fetal bovine serum (FBS), antibiotic, PBS (phosphate buffered saline), Trizol, and a Lipofectamine 2000 reagent were purchased from Invitrogen Co. (Carlsbad, Calif.).

An MTT assay kit, pVMC luciferase plasmid, luciferase assay system were purchased from Promega Co. (Madison, Wis.), and jetPEI was purchased from Polyplustransfection Co. (New York, N.Y.).

A first strand cDNA synthesis kit and Taq DNA polymerase were purchased from Takara Bio Inc. (Shiga, Japan), Anti-pVMC-Luc siRNA (siLuc) (5'-UUGUUUUGGAGC-GAAAdTdT-3' (sense) of SEQ ID NO. 1 and 5'-UUUCGCUCCAAAACAAdTdT-3' (antisense) of SEQ ID NO. 2), anti-VEGF siRNA (siVEGF) (5'-AUGUGAAUG-CAGACCAAAGAATTdTdT-3' (sense) of SEQ ID NO. 3 and 5'-UUCUUUGGUCUGCAUUCACAATTdTdT-3' (antisense) of SEQ ID NO. 4), and antiapolipoprotein B siRNA, siApoB (5'-GUCAUCACACUGAAUACCAAUdTdT-3' (sense) of SEQ ID NO. 5 and 5'-AUUGGUAUUCAGU-GUGAUGACdTdT-3' (antisense) of SEQ ID NO. 6) were purchased from Bioneer Co. (Daejun, Republic of Korea). All the reagents were used without further purification.

EXAMPLE 1

Preparation of a Composite for Nucleic Acid Delivery by Sequential Self Assembly of Nucleic Acid, Polyethyleneimine (PEI), Hyaluronic Acid (HA) on Cysteamine Introduced Gold Nanoparticles <1-1> Synthesis of Cysteamine Introduced Gold Nanoparticles (AuCM)

A method of synthesizing positive charge (cysteamine) introduced gold nanoparticles (AuCM) according to one embodiment of the invention is schematically shown in FIG. 1.

According to the method of FIG. 1, 80 mL (1.4 mM) of a $HAuCl_4$ aqueous solution was dissolved in distilled water together with 800 μL (0.2M) of a cysteamine hydrochloride aqueous solution for 20 minutes, 2 ml (1 mM) of a $NaBH_4$ aqueous solution was added dropwise as a reducing agent, and they were reacted with agitation at room temperature for 12 hours to synthesize cysteamine introduced gold nanoparticles (AuCM). And then, the synthesized product was filtered and purified using a filter tube (cutoff 10000 Da) in distilled water for 12 hours to preparer cysteamine introduced gold nanoparticles (AuCM).

Figure 4:
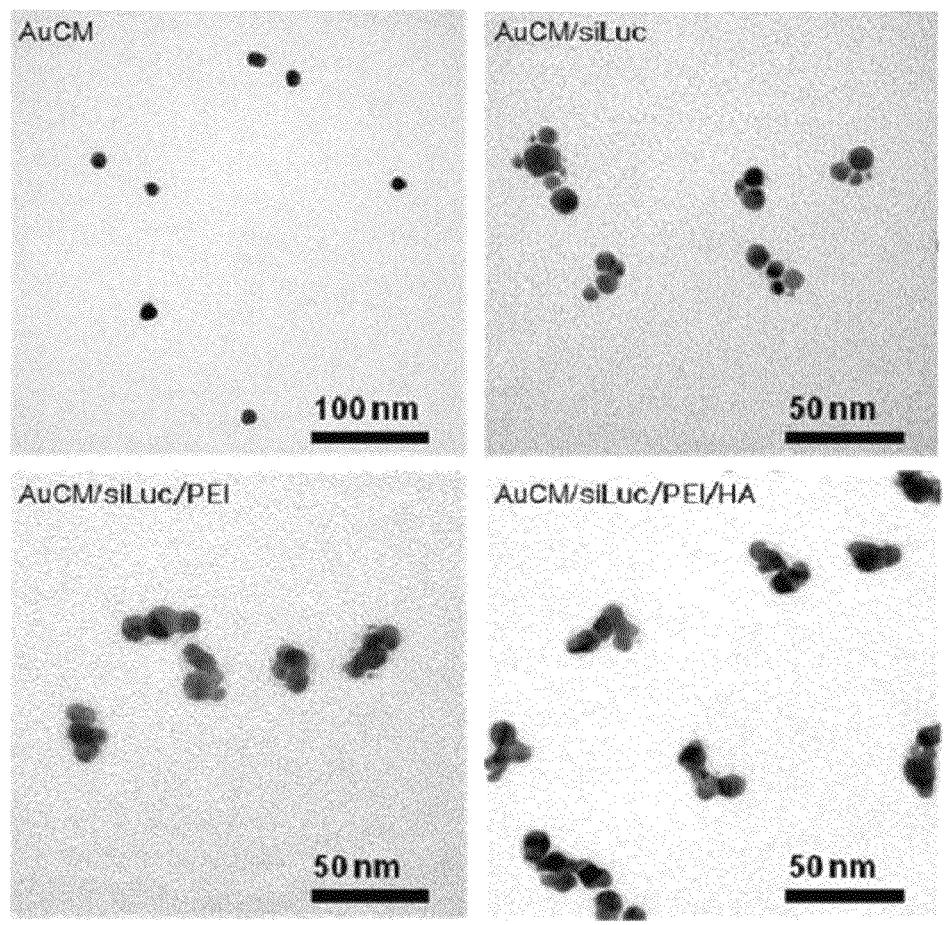
FIG. 4 shows the results of analyzing AuCM, AuCM/siLuc, AuCM/siLuc/PEI, and AuCM/siLuc/PEI/HA composites prepared according to <Example 1> by TEM.
Figure 7:
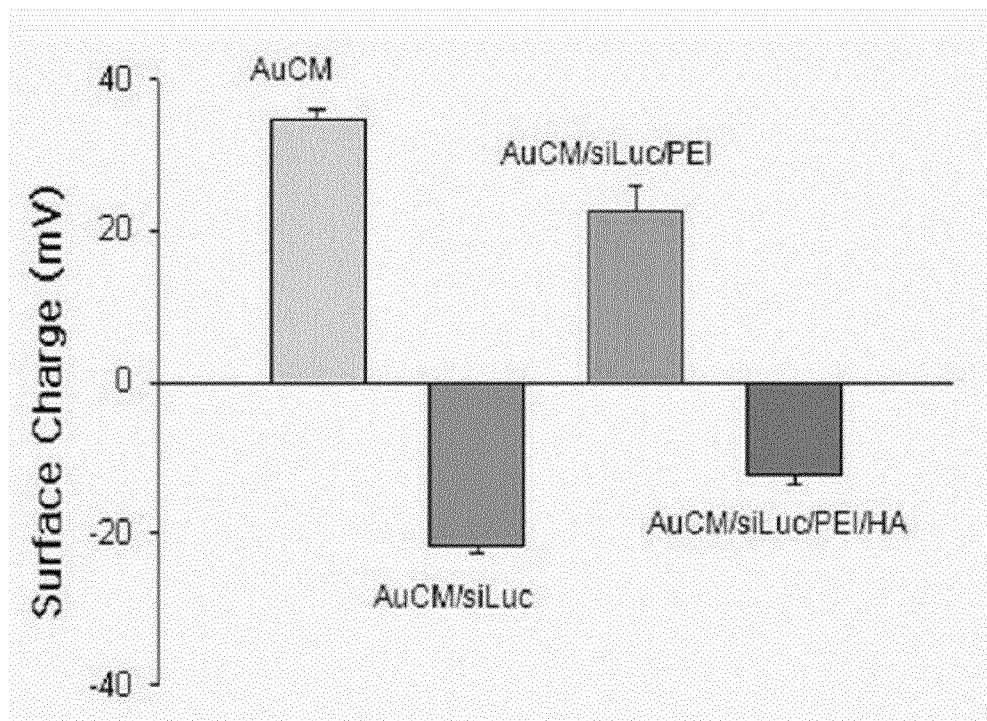
FIG. 7 shows the results of analyzing AuCM, AuCM/siLuc, AuCM/siLuc/PEI, and AuCM/siLuc/PEI/HA composites prepared according to <Example 1> with zeta potential analyzer.

It was confirmed whether or not gold nanoparticles AuCM were synthesized using TEM (transmission electron microscopy) (Hitachi, Tokyo, Japan) and zeta potential analyzer (Zetasizer Nano, Malvern Instrument Co., UK), and the TEM results and surface charge measurement results are respectively shown in FIG. 4 and FIG. 7.

As shown in FIG. 4 (left upper part) and FIG. 7, it was confirmed from the TEM results that gold nanoparticles having about 13 nm diameter were synthesized, and the analysis results of zeta potential analyzer showed that the synthesized gold nanoparticles have about +35 mV surface charge, thus confirming that positive charge was introduced.

<1-2> Formation of AuCM/siRNA/PEI/HA Composite

Figure 3A:
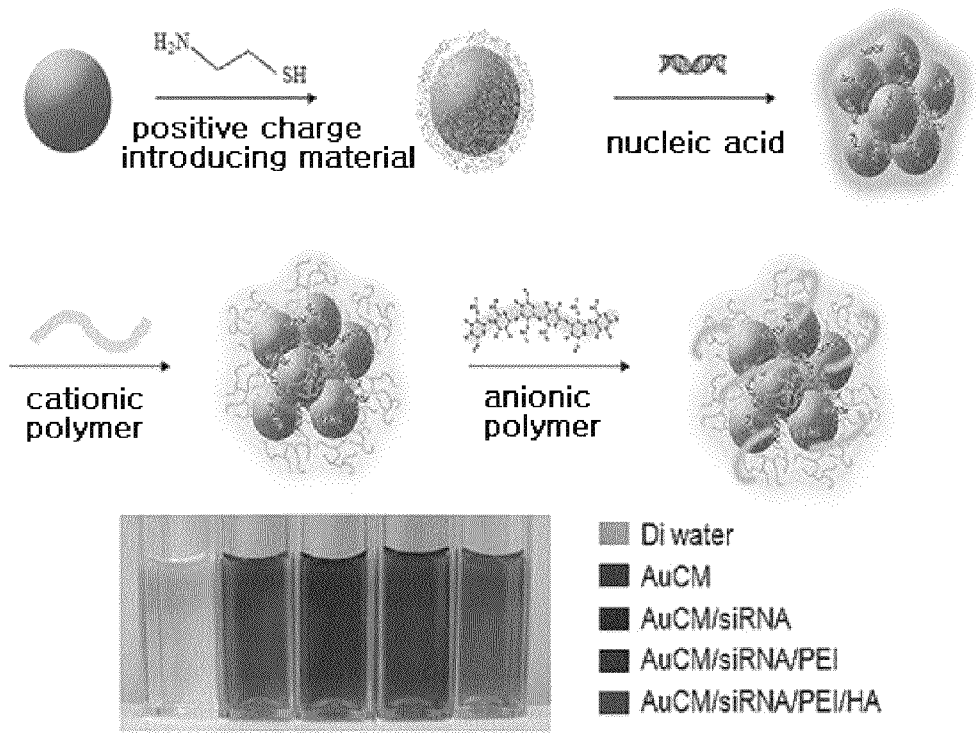
FIG. 3 schematically shows a method of forming an AuCM/siRNA/PEI/HA composite by sequentially coating siRNA, PEI, HA on AuCM using electrostatic attraction according to <Example 1> (FIG. 3a), and the structure of the prepared composite (FIG. 3b).
Figure 3B:
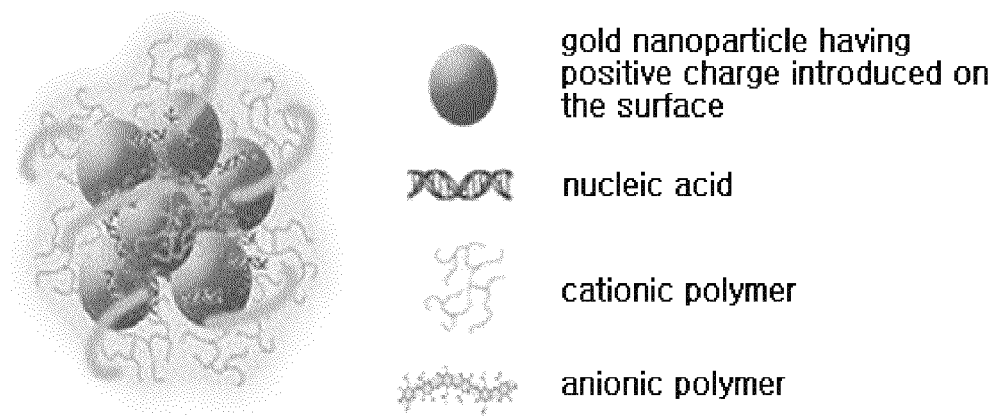

As shown in FIG. 3a, a AuCM/siRNA/PEI/HA composite was prepared by sequentially coating siRNA, PEI, HA on AuCM synthesized in <Example 1-1> by layer-by-layer method.

A. Formation of AuCM/siRNA Composite and Optimization of Mole Ratio of AuCM to siRNA An AuCM/siRNA composite was prepared, and the mole ratio of AuCM to siRNA was optimized for high binding efficiency of siRNA and high stability of the prepared AuCM/siRNA composite. As the siRNA, siLuc was used.

The $Au^{3+}$ concentration of the AuCM aqueous solution was 0.14 mg/mL, as measured using ICP-AES (Inductively coupled plasma atomic emission spectroscopy) (ICAP 6000 series, Thermo scientific, Seoul, Korea), and based thereon, molarity of the AuCM aqueous solution was calculated by a reported equation (*Colloids Surf B Biointerfaces* 2007, 58, 3-7.) (10.45 nM).

Figure 2:
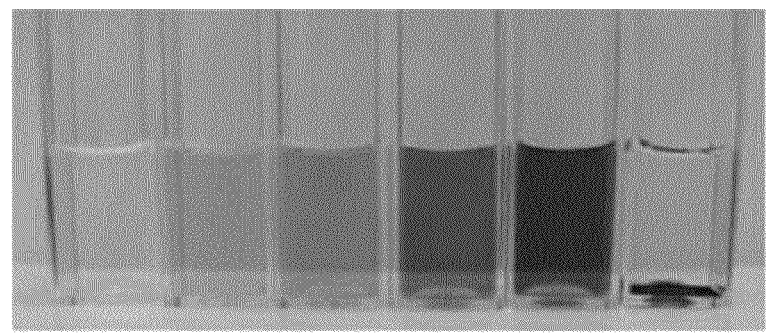
FIG. 2 shows a photograph of the solutions as the ratio of AuCM to siLuc increases according to <Example 1-2> (top image: farthest to the right represents distilled water, and from the right, solutions wherein the mole ratio of AuCM to siLuc is increased to 2.6, 5.2, 10.4, 15.7 and $20.8 \times 10^{-2}$ are sequentially represented), and the results of quantifying the amount of siLuc forming a composite as the ratio of AuCM to siLuc increases by measuring UV-Vis absorbance at 260 nm (bottom graph).
Figure 2:
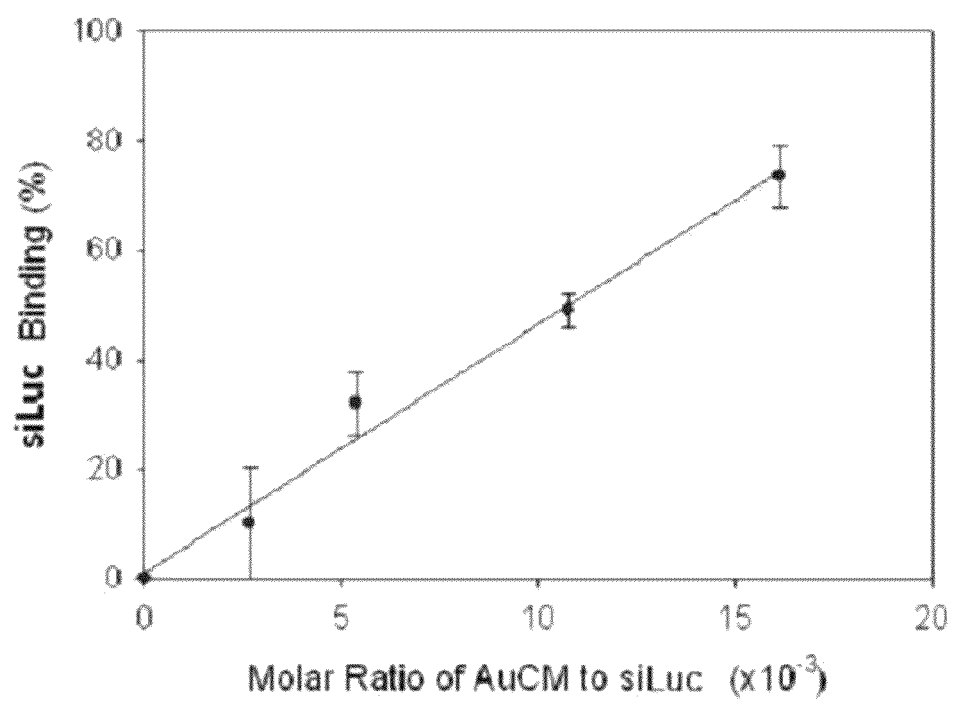

To the siLuc aqueous solution, AuCM aqueous solutions of various molarities calculated by the above method were introduced, and the mixed solutions were purified with a centrifuge (15000 g, 15 minutes) after 1 hour to prepare AuCM/siLuc composites, which are respectively shown in FIG. 2

As shown in FIG. 2, if the molarity of AuCM to siLuc is beyond a certain concentration, precipitation occurs. The top image of FIG. 2 is a photograph of the solutions with gradually increasing the mole ratio of AuCM to siRNA (siLuc), wherein from the right, distilled water, and solutions respectively having mole ratios of AuCM to siRNA of 2.6, 5.2, 10.4, 15.7 and $20.8 \times 10^{-2}$ are shown. It can be seen that if the mole ratio of AuCM/siRNA is equal to or less than $15.7 \times 10^{-2}$, the composite is well dispersed without precipitation, but if it is equal to or more than $20.8 \times 10^{-2}$, precipitation occurs and settles to the bottom. Therefore, it is confirmed that the molarity of AuCM to siLuc where nucleic acid may be maximum bound while minimizing loss of nucleic acid without precipitation is about $15.7 \times 10^{-2}$.

The binding efficiency of siLuc to AuCM was analyzed by precipitating the AuCM/siLuc composite with a centrifuge, and then, measuring UV-Vis absorbance of the supernatant at 260 nm with Uvikon 941 spectrophotometer (Kontron Instruments GmbH, Germany). The concentration of siLuc was calculated using a standard curve of siLuc, and the siLuc participating in the formation of the AuCM/silLuc composite was quantitatively analyzed. As the mole ratio of AuCM to siLuc increases, the amount of siLuc that remains in the supernatant decreases, which means that the amount of siLuc participating in the formation of the AuCM/siLuc composite increases. And, as can be seen from the graph in the bottom of FIG. 2, the amount of siLuc participating in the formation of the AuCM/siLuc composite at a mole ratio of $15.7 \times 10^{-2}$, which was confirmed to be an optimum mole ratio of AuCM to siLuc, is about 70%, thus confirming very excellent binding efficiency. The optimum mole ratio may be applied without limitations to the kind of siRNA, and although the binding efficiency of each siRNA to the metal particles may slightly differ according to the sequence length of the used siRNA, it does not influence on the effect.

B. Formation of AuCM/siRNA/PEI/HA Composite

First, a AuCM aqueous solution was introduced in a siLuc aqueous solution such that the mole ratio of AuCM to siRNA may become $1.57 \times 10^{-2}$, which was confirmed as optimized mole ratio according to the A, and after 1 hour, the solution was purified using a centrifuge (15000 g, 15 minutes). The purified AuCM/siLuc composite aqueous solution was dispersed in a PEI aqueous solution (1 mg/mL), and after 30 minutes, purified with a centrifuge (15000 g, 15 minutes) to prepare an AuCM/siLuc/PEI complex. The supernatant was analyzed by ATTO-TAG CBQCA amine-derivatization kit (Invitrogen Co., Carlsbad, Calif.) according to the manufacturer's instructions to quantitatively analyze PEI participating in the formation of the AuCM/siLuc/PEI complex. As the result, it was confirmed that about 0.5% of the introduced PEI amount participated in the formation of the AuCM/siLuc/PEI composite, and the N/P ratio of PEI to siLuc was shown to be about 3.6

The purified AuCM/siLuc/PEI composite aqueous solution was dispersed in a HA aqueous solution (4 mg/mL), and after 30 minutes, purified with a centrifuge (15000 g, 15 minutes) to finally prepare an AuCM/siLuc/PEI/HA composite. Through the analysis of carbazole in the supernatant, HA participating in the formation of the AuCM/siLuc/PEI/HA composite was quantitatively analyzed (see Song, J.-M.; Im, J.-H.; Kang, J.-H.; Kang, D.-J. A Simple Method for Hyaluronic Acid Quantification in Culture Broth. Carbohydr. Polym. 2009, 78, 633-634). As the results of quantitative analysis, it was confirmed that about 1.7% of the introduced HA amount participated in the formation of the AuCM/siLuc/PEI/HA composite, and the mass ratio of HA to PEI was about 15.7 and the charge ratio was about 1.6.

EXPERIMENTAL EXAMPLE 1

Confirmation of Formation of AuCM/siRNA/PEI/HA Composite and Analysis

The AuCM/siLuc/PEI/HA composite prepared according to <Example 1> was analyzed using TEM (transmission electron microscopy) (Hitachi, Tokyo, Japan), AFM (atomic force microscopy) (VEECO Instrument Co., New York, N.Y.), DLS (dynamic light scattering) (Zetasizer Nano, Malvern Instrument Co., UK), zeta potential analyzer, and UV-vis spectrophotometer (S-3100, Scinco Co., Seoul, Korea), and the results are shown in FIG. 4 to FIG. 8, respectively.

As shown in the TEM results of FIG. 4, it was confirmed that in the AuCM/siLuc composite, several AuCM gathered to form a cluster (right upper part of FIG. 4), and PEI and HA coated the AuCM/siLuc cluster (left lower part and right lower part of FIG. 4).

Figure 5:
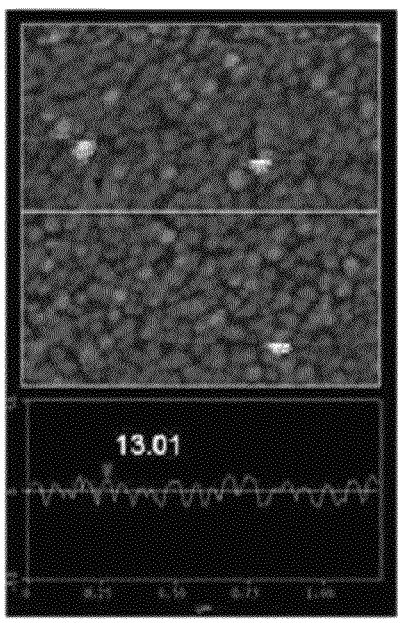
FIG. 5 shows the results of analyzing AuCM, AuCM/siLuc, AuCM/siLuc/PEI, and AuCM/siLuc/PEI/HA composites prepared according to <Example 1> by AFM.
Figure 5:
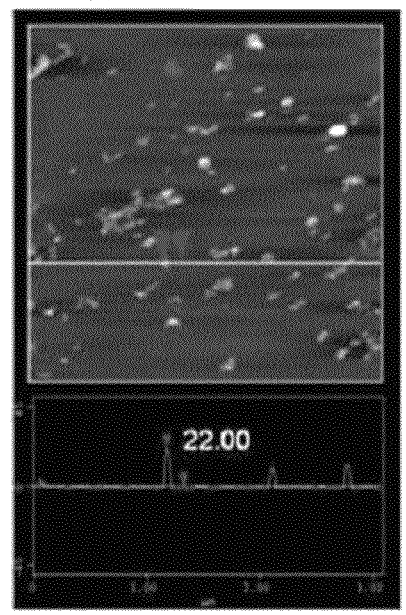
Figure 5:
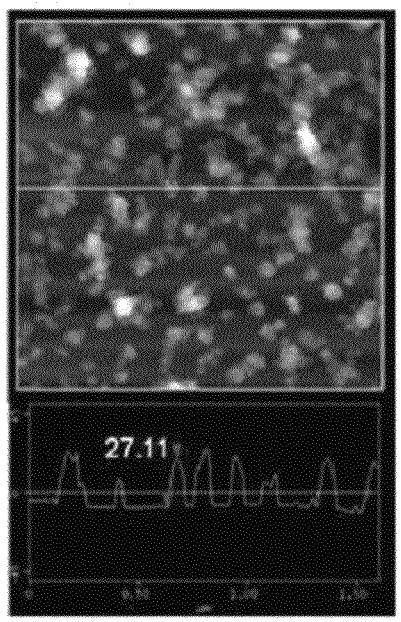
Figure 5:
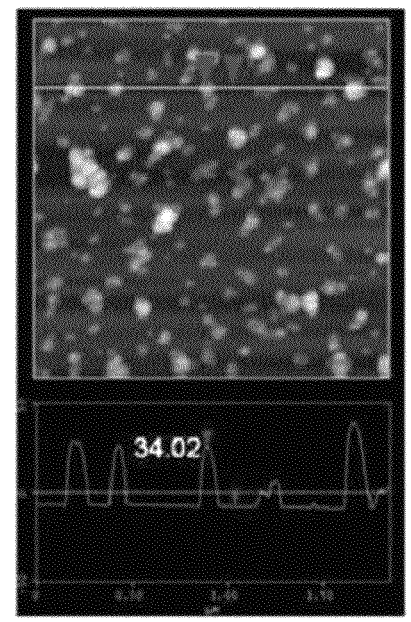
Figure 6A:
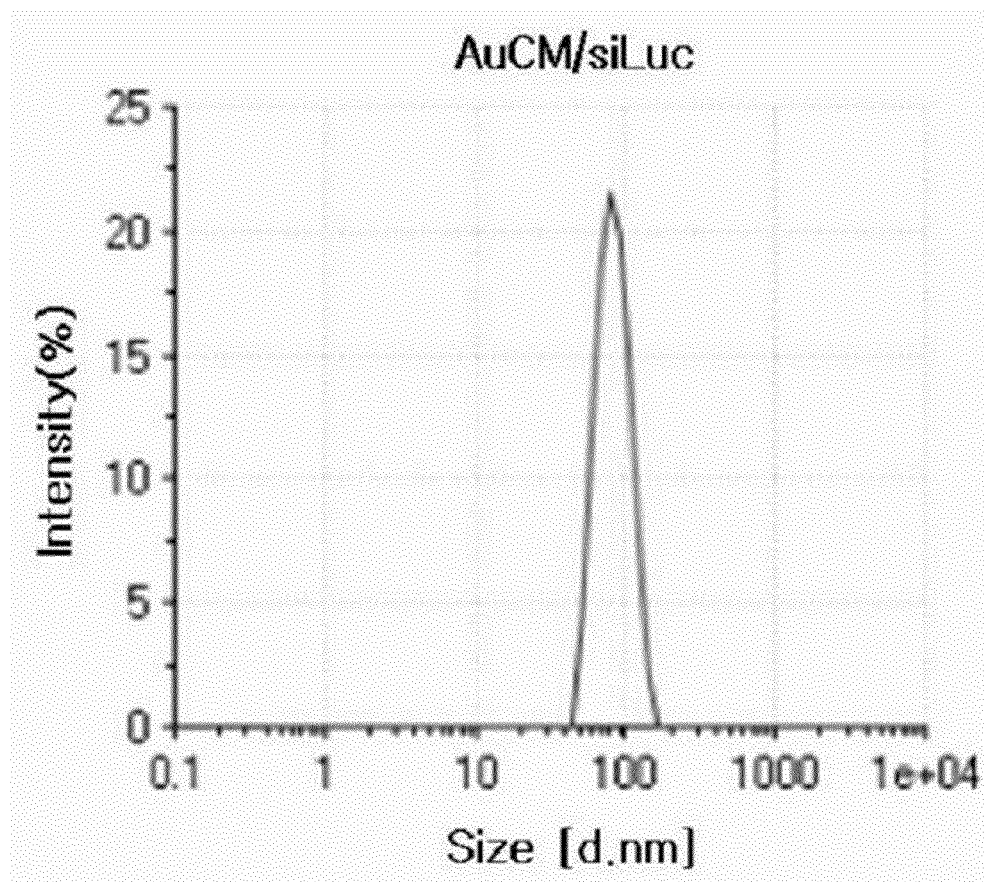
FIGS. 6a to 6d shows the results of analyzing AuCM, AuCM/siLuc, AuCM/siLuc/PEI, and AuCM/siLuc/PEI/HA composites prepared according to <Example 1> by DLS.
Figure 6B:
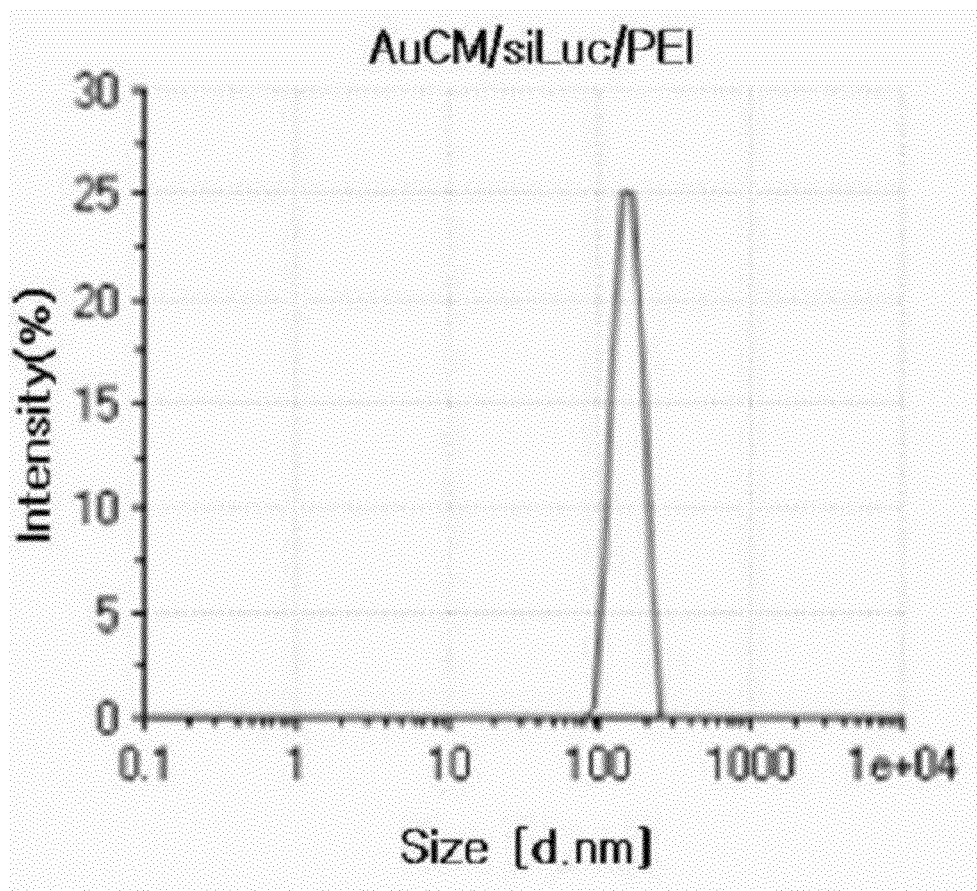
Figure 6C:
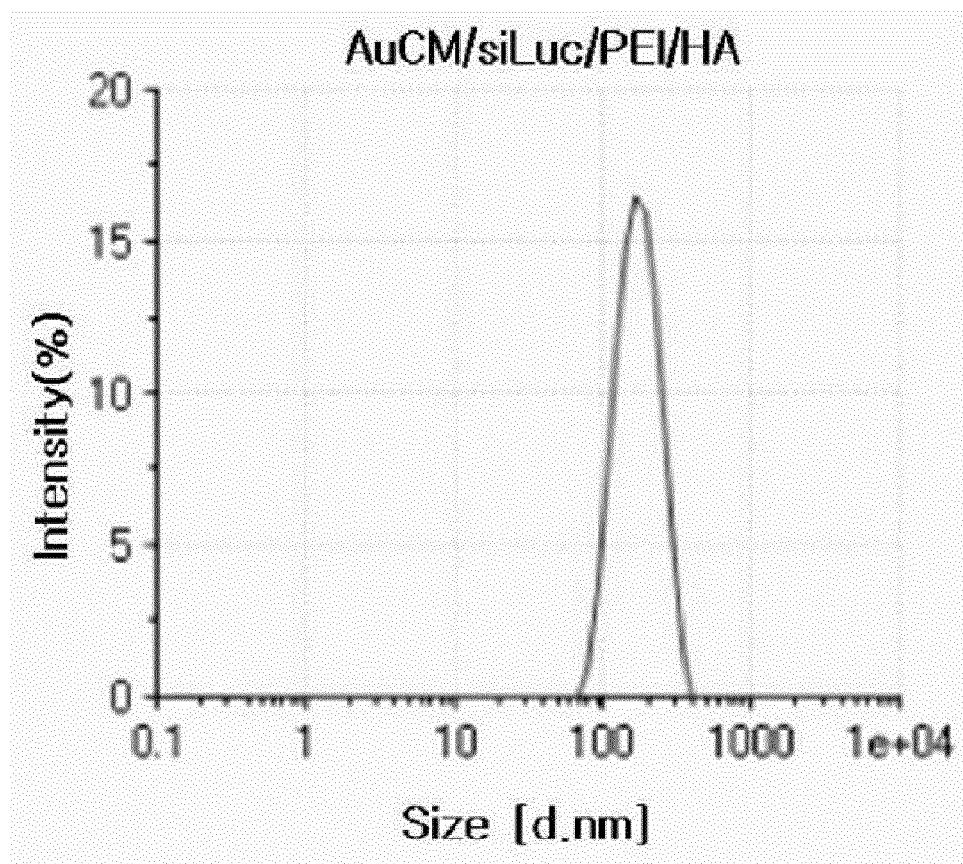
Figure 6D:
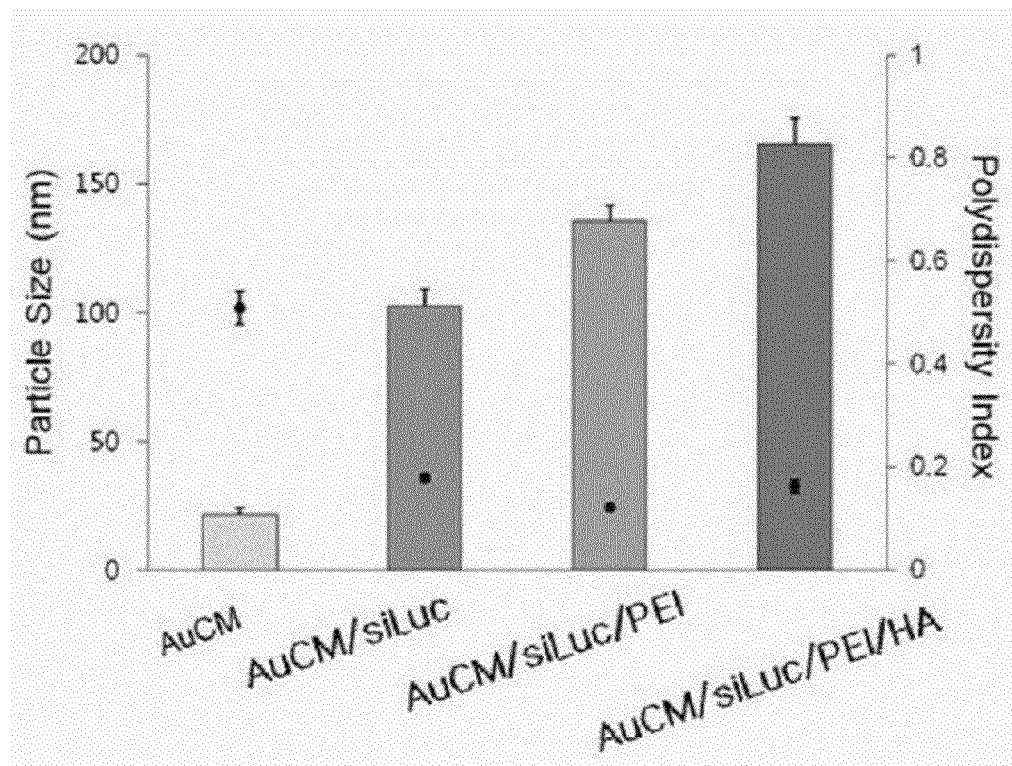

And, by measuring the height of the particle from the AFM image of FIG. 5, it was confirmed that the sizes of AuCM, AuCM/siLuc, AuCM/siLuc/PEI, and AuCM/siLuc/PEI/HA increase to 13.8±3.2 nm, 27.13±8.9 nm, 33.06±10.5 nm, and 37.25±8.8 nm, respectively. And as the result of measuring hydrodynamical diameter by DLS, it was confirmed that the sizes of AuCM, AuCM/siLuc, AuCM/siLuc/PEI, and AuCM/siLuc/PEI/HA increase to 21.37±3.2 nm, 104.9±6.6 nm, 137.7±5.6 nm, and 165.47±9.9 nm, respectively, and thus, it can be seen that the self assembled composite according to one example of the invention has a single zeta size peak and the dispersion is measured uniformly (FIG. 6*a* to FIG. 6*d*).

Figure 8:
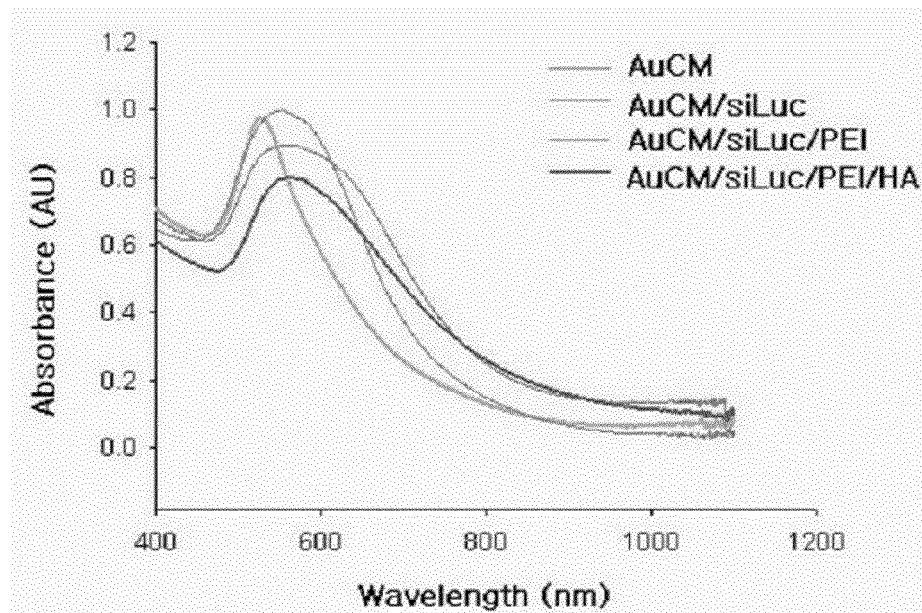
FIG. 8 shows the results of analyzing AuCM, AuCM/siLuc, AuCM/siLuc/PEI, and AuCM/siLuc/PEI/HA composites prepared according to <Example 1> with UV-Vis absorbance spectra.

And, as shown in the measurement results of surface charge using Zeta potential analyzer in FIG. 7, the surface charges of AuCM, AuCM/siLuc, AuCM/siLuc/PEI, and AuCM/siLuc/PEI/HA are respectively +34.85±1.3 mV, −21.6±0.8 mV, +22.5±3.3 mV, and −12.1±1.5 mV, thus confirming that positive charge and negative charge are alternated. And, through the red shift of UV-vis spectra in FIG. 8, the result supporting the TEM image of FIG. 4 was confirmed (FIG. 8).

EXPERIMENTAL EXAMPLE 2

Toxicity Evaluation of AuCM/siRNA/PEI/HA Composite

To examine toxicity of the AuCM/siLuc, AuCM/siLuc/PEI and AuCM/siLuc/PEI/HA prepared in <Example 1>, MTT assay was conducted.

Specifically, B16F1 cells that were cultured in a DMEM medium (GIBCO-BRL, NY, USA) containing 10% (v/v) fetal bovine serum and 100 U/mL penicillin-streptomycin were divided into 96-well plate, and cultured at 37° C., 5% $CO_2$ until the cells grow to about 70% of the plate. And then, the AuCM/siLuc, AuCM/siLuc/PEI and AuCM/siLuc/PEI/HA prepared in <Example 1> were introduced into each well at various siLuc concentrations, and the cells were cultured at 37° C., 5% $CO_2$ for 24 hours. And then, cytotoxicity was measured by MTT assay, and the results are shown in FIG. 9 (control: non-treated group).

Figure 9:
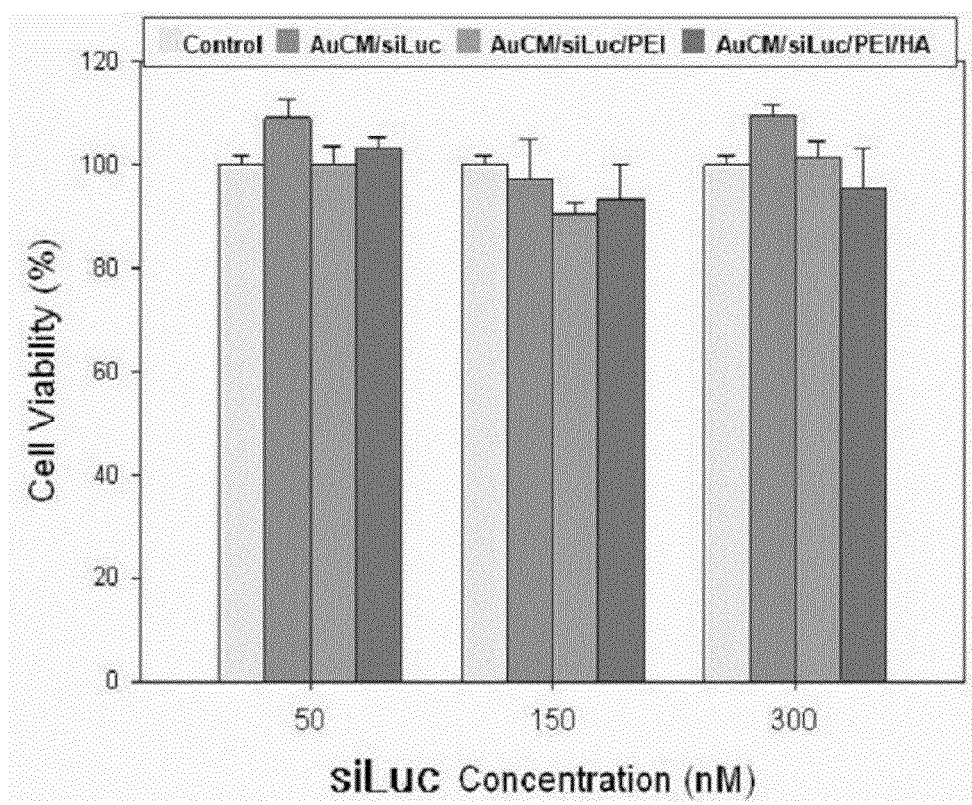
FIG. 9 shows the results of analyzing the cytotoxicity (survival rate in B16F1) of AuCM/siLuc, AuCM/siLuc/PEI, AuCM/siLuc/PEI/HA according to <Experimental Example 2>.

As shown in FIG. 9, it can be seen that all the AuCM/siLuc, AuCM/siLuc/PEI and AuCM/siLuc/PEI/HA composites had little cytotoxicity.

EXPERIMENTAL EXAMPLE 3

Evaluation of Stability of AuCM/siRNA/PEI/HA Composite

Figure 10:
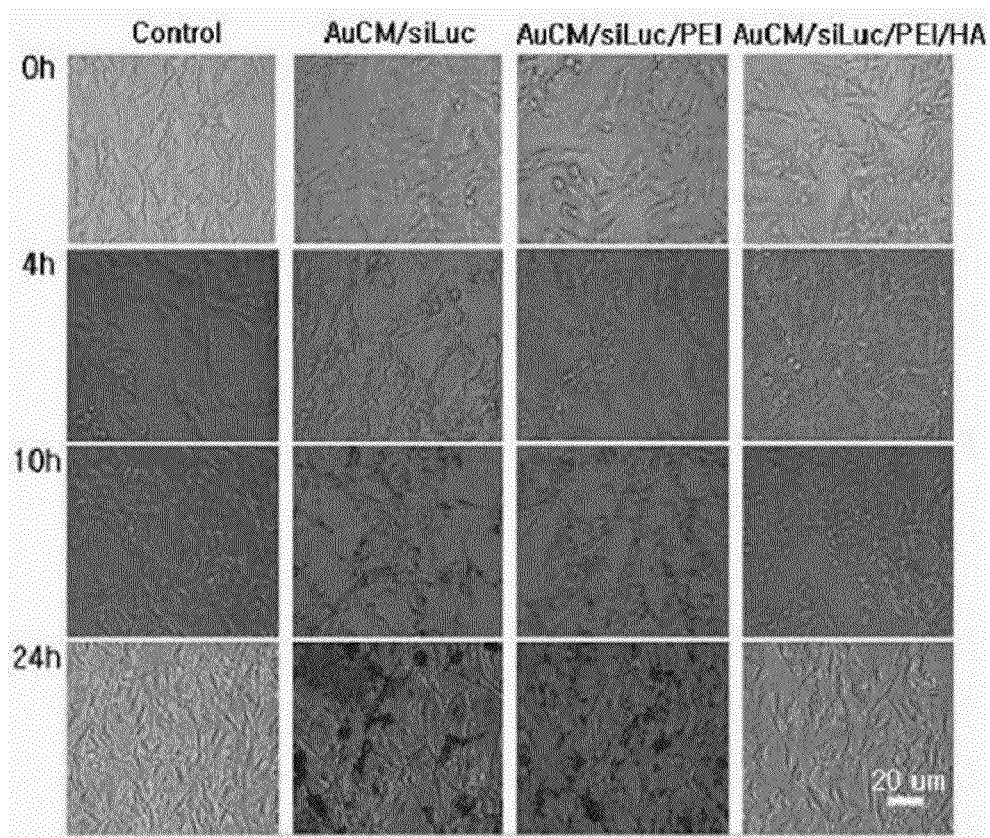
FIG. 10 is optical microscope images showing particle stabilities of AuCM/siLuc, AuCM/siLuc/PEI, AuCM/siLuc/PEI/HA when cultured in a cell culture medium containing serum together with B16F1 cells according to <Experimental Example 3>.

To examine stabilities of the AuCM/siLuc, AuCM/siLuc/PEI, and AuCM/siLuc/PEI/HA composites prepared in <Example 1>, B16F1 cells that were cultured in DMEM medium containing 50% (v/v) fetal bovine serum and 100 U/mL penicillin-streptomycin were treated with each AuCM/siLuc, AuCM/siLuc/PEI, and AuCM/siLuc/PEI/HA composite at siLuc concentration of 100 nM, and changes were observed with microscope over time and shown in FIG. 10.

As shown in FIG. 10, although AuCM/siRNA, and AuCM/siRNA/PEI composites showed precipitations over time, AuCM/siRNA/PEI/HA composite maintained stable without precipitation even after 24 hours, thus confirming that it has very excellent serum stability, i.e., stability in the body.

EXPERIMENTAL EXAMPLE 4

Evaluation of Intracellular Uptake of AuCM/siRNA/PEI/HA Composite

To examine intracellular uptake of the AuCM/siLuc, AuCM/siLuc/PEI, AuCM/siLuc/PEI/HA composite prepared in <Example 1>, B16F1 cells were divided into 100-mm cell culture dish, and cultured in DMEM medium containing 50% (v/v) fetal bovine serum and 100 U/mL penicillin-streptomycin until they occupied about 90% of the area, and then, treated with each AuCM/siLuc, AuCM/siLuc/PEI, and AuCM/siLuc/PEI/HA composite at siLuc concentration of 100 nM. After 24 hours, the cells were washed with PBS three times, and then, detached, and pelletized using a centrifuge (1000×g, 3 minutes). It was fixed in cacodylate buffer with 2% (w/v) glurataldehyde for 12 hours, and then, washed with 0.1 M cacodylate buffer, and fixed with osmium tetroxide at 4° C. for 100 minutes. And then, it was washed with 0.1 M cacodylate buffer many times, and each sample was put into agarose and dehydrated in ethanol (70, 80, 90, 95 and 100 vol %). It was put into Epon (SPI-Pon™ 812 Epoxy Embedding Kit, Structure Probe, Inc., West Chester, Pa.), and cut into thin to a thickness of about 70 nm, which was confirmed by TEM and shown in FIG. 11.

Figure 11:
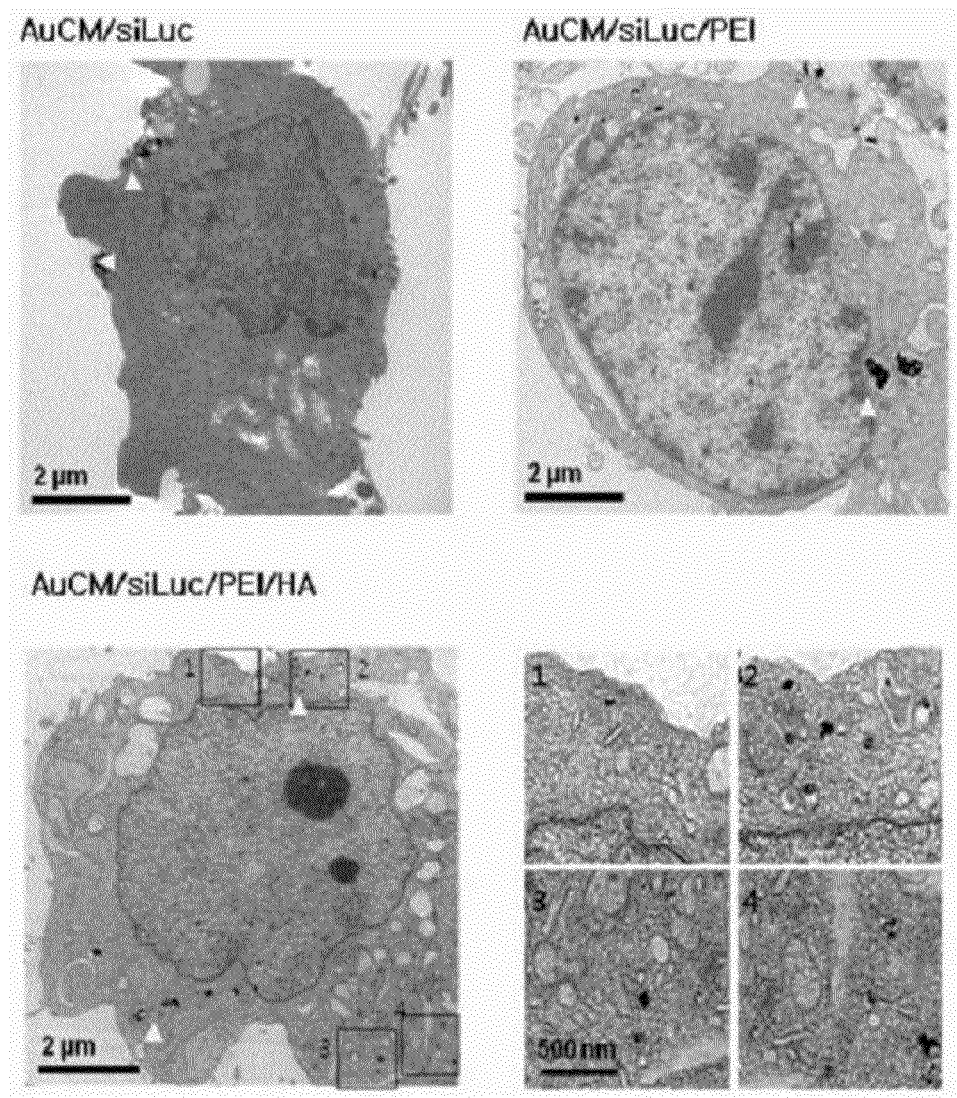
FIG. 11 shows the results of analyzing uptake of AuCM/siLuc, AuCM/siLuc/PEI, AuCM/siLuc/PEI/HA in B16F1 cells by TEM according to <Experimental Example 4>

As shown in FIG. 11, it was confirmed that AuCM/siLuc, AuCM/siLuc/PEI composites are attached to cell wall or uptaken in the cells in the aggregated state, while AuCM/siLuc/PEI/HA composite is uniformly distributed in the cytoplasm.

EXPERIMENTAL EXAMPLE 5

Gene silencing activity evaluation of AuCM/siRNA/PEI/HA composite

Gene silencing activity of AuCM/siRNA/PEI/HA composite was evaluated by co-transfection (see Kim et al., Bioconj. Chem. 17 (2006) 241-244, Lee et al., J. Control. Release 119 (2007) 245-252 and Park et al., Biomaterials 31 (2010) 5258-5265).

First, AuCM/siLuc, AuCM/siLuc/PEI, and AuCM/siLuc/PEI/HA composites were prepared according to Example 1 using Anti-pVMC-Luc siRNA (siLuc) (SEQ ID NOs. 1 and 2) as siRNA.

Figure 12A:
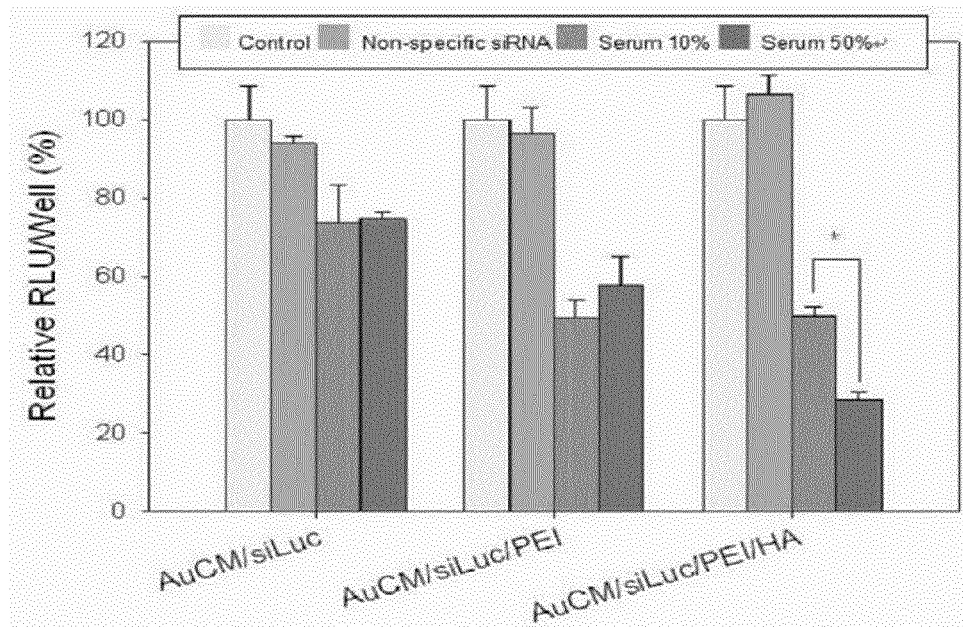
FIG. 12a shows the results of observing the effect for inhibiting Luciferase protein of the AuCM/siLuc/PEI/HA composite using PGL3-Luc reporter gene in B16F1 cells according to <Experimental Example 5>.

B16F1 cells were divided into 24 well plate at 2×10⁴ per well, and cultured at 37 t for 24 hours, and then, jetPEI/PGL3-Luc composite (jetPEI™, Polyplus-transfection Co., New York, N.Y.) was introduced, and the cells were cultured at 37° C. and 5% CO$_2$ for 3 hours, and then, washed with PBS. And then, the cells were treated with each sample (AuCM/siLuc, AuCM/siLuc/PEI, and AuCM/siLuc/PEI/HA composites) at siLuc concentration of 100 Nm, and cultured at 37° C. and 5% CO$_2$ for 24 hours in DMEM medium containing 10% or 50% fetal bovine serum and 100 U/mL penicillin-streptomycin. And then, Luciferase activity was measured for 30 seconds with Luminometer at excitation wavelength of 486 nm and emission wavelength of 538 nm, using luciferase assay system (Promega Co. (Madison, Wis.) according to the manufacturer's instructions, and the results are shown in FIG. 12a.

Next, AuCM/siVEGF/PEI/HA composite was prepared using Anti-VEGF siRNA (siVEGF) (SEQ ID NOs. 3 and 4) according to <Example 1>, and inhibition of gene expression was evaluated.

Specifically, B16F1 cells were divided into 6 well plate at 1×10⁵ per well, and cultured at 37° C., 5% CO$_2$ for 24 hours, and then, treated with each sample (AuCM/siLuc/PEI/HA composite, Lipofectamine/siVEGF (Lipofectamine™ 2000 Transfection Reagent, Invitrogen Co. Carlsbad, Calif., prepared according to the manufacturer's instructions), and AuCM/siVEGF/PEI/HA composite) at siVEGF concentration of 100 nM in DMEM medium containing 50% fetal bovine serum and 100 U/mL penicillin-streptomycin. After 24 hours, cell wall was dissolved with trizol, and RNA was extracted.

Figure 12B:
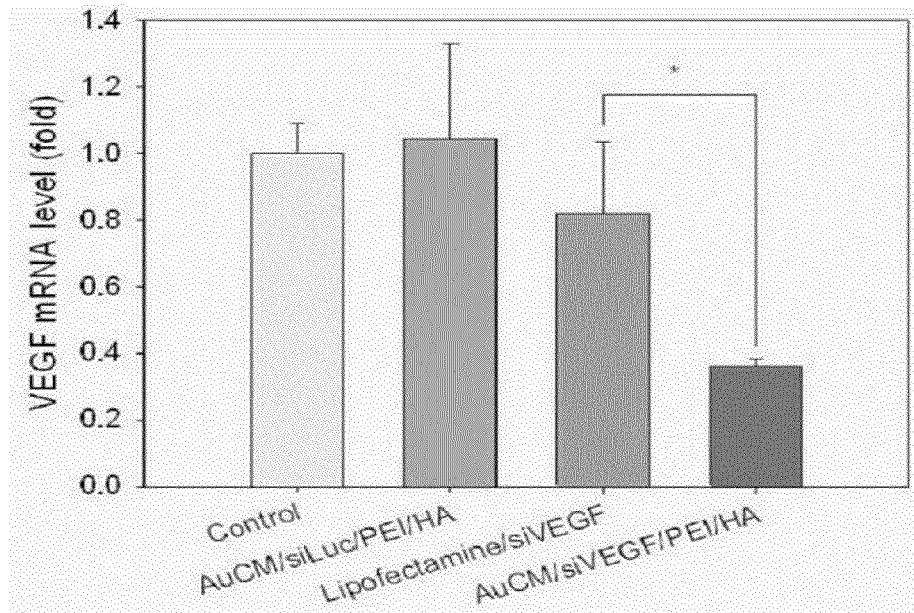
FIG. 12b shows the results of observing the effect for inhibiting VEGF mRNA of the AuCM/siVEGF/PEI/HA composite in B16F1 cells according to <Experimental Example 5>.

1 µg of the extracted RNA was reverse-transcribed to synthesize cDNA using a first strand cDNA synthesis kit according to the manufacturer's instructions, and VEGF mRNA level was normalized to GAPDH mRNA level at serum concentration of 50 vol %, by RT-PCR (initial denaturation at 95° C. for 5 minutes, followed by 40 cycles of 95° C. for 30 seconds and 53° C. for 30 seconds) using Taq DNA polymerase, which is shown in FIG. 12b. The sequences of the used primers are as follows.

```
<GAPDH primer>
Forward direction:
                                  (SEQ ID NO.: 7)
5'-AGGCCGGTGCTGAGTATGTC-3'

Reverse direction:
                                  (SEQ ID NO.: 8)
5'-TGCCTGCTTCACCACCTTCT-3'

<VEGF primer>
Forward direction:
                                  (SEQ ID NO.: 9)
5'-GGAGATCCTTCGAGGAGCACTT-3'

Reverse direction:
                                  (SEQ ID NO.: 10)
5'-GGCGATTTAGCAGCAGATATAAGAA-3'
```

As shown in FIG. 12a, AuCM/siLuc composite exhibited 75% or more luciferase activity at low serum concentration of 10 vol % as well as at serum concentration of 50 vol %, and thus, had relatively low luciferase activity inhibition effect, and AuCM/siLuc/PEI composite inhibited luciferase activity to about 50% at low serum concentration, but exhibited lowered luciferase activity inhibition effect at high serum concentration of 50 vol %.

On the other hand, AuCM/siLuc/PEI/HA composite exhibited about 50% luciferase activity inhibition effect at low serum concentration of 10 vol %, and exhibited higher inhibition effect (decreased luciferase activity about 70% or more) at high serum concentration of 50 vol %. Thus, it was confirmed that the AuCM/siLuc composite which delivers nucleic acid using metal nanoparticles only and the AuCM/siLuc/PEI composite which delivers nucleic acid using metal nanoparticles and cationic polymer exhibit decreased intracellular nucleic acid delivery efficiency as serum concentration increases, while the AuCM/siLuc/PEI/HA composite prepared according to one example of the invention exhibits more increased luciferase activity inhibition effect, namely intracellular nucleic acid delivery efficiency, as serum concentration increases, and thus, has very excellent serum stability.

And, as shown in FIG. 12b, at high serum concentration of 50 vol %, the Lipofectamine/siVEGF composite inhibited VEGF mRNA level about 20%, while the AuCM/siVEGF/PEI/HA composite inhibited VEGF mRNA level about 70% or more, exhibiting 3.5 times or more VEGF mRNA level inhibition effect than the Lipofectamine/siVEGF composite, and thus, it was confirmed that the AuCM/siVEGF/PEI/HA composite very effectively inhibits VEGF mRNA level at high serum concentration. Meanwhile, the AuCM/siLuc/PEI/HA composite did not inhibit VEGF mRNA level at all, and thus, it was confirmed that the AuCM/siRNA/PEI/HA composite prepared in <Example 1> specifically acts on targeted gene.

As explained, it can be seen that the AuCM/siRNA/PEI/HA composite prepared in <Example 1> has remarkably excellent silencing activity of targeted gene, and it is confirmed that since the excellent gene silencing activity increases more at high serum concentration, the AuCM/siRNA/PEI/HA composite is very useful as system for application in the body.

EXPERIMENTAL EXAMPLE 6

Evaluation of Target Directed Cellular Uptake of AuCM/siRNA/PEI/HA Composite

To examine if target directed intracellular uptake of the AuCM/siLuc/PEI/HA composite prepared in <Example 1> is intermediated by HA receptor, the following experiment was conducted.

Specifically, B16F1 cells having HA receptor were divided into 8 well culture slide at 1×10⁴ per well, cultured 37° C. and 5% $CO_2$ for 24 hours, and then, cultured at 37° C. and 5% $CO_2$ for 1 hour in DMEM medium containing 50% fetal bovine serum and 100 U/mL penicillin-streptomycin with/without HA (2 mg/mL). And then, the cells were treated with the AuCM/siLuc/PEI/HA composite at siLuc concentration of 100 nM, and cultured at 37° C. and 5% $CO_2$ for 24 hours. The medium was removed, the cells were washed with PBS three time, fixed with 4 vol % paraformaldehyde, and then, analyzed by dark field bioimaging (Axioplan 2 Microscope, Carl Zeiss, Germany) (see Nam et al., J. Am. Chem. Soc. 131 (2009) 13639-13645), and shown in FIG. 13 (In FIG. 13, 'a' represents non-treated cells; 'b' represents cells treated with AuCM/siLuc/PEI/HA composite in a medium without extra HA; 'c' represents cells treated with AuCM/siLuc/PEI/HA composite and extra HA; and, 'd' is enlarged view of 'b').

Figure 13:
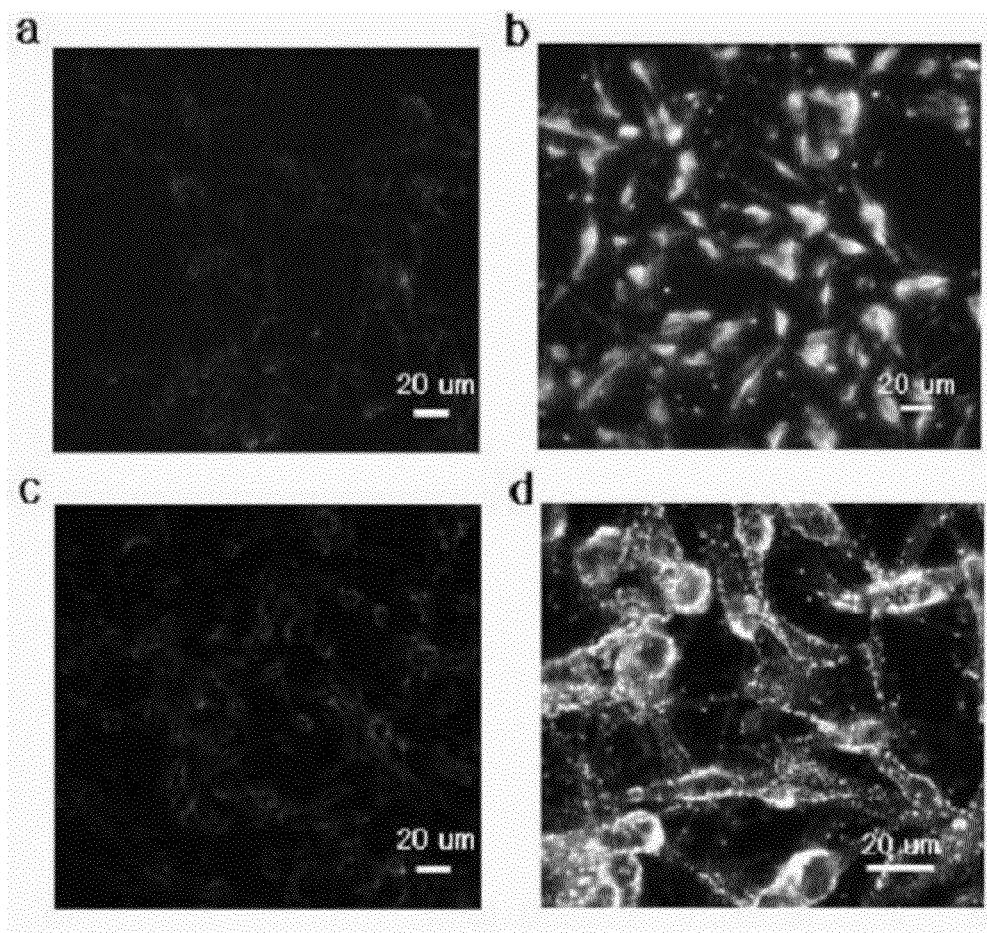
FIG. 13 shows the results of observing cellular uptake of AuCM/siLuc/PEI/HA in B16F1 cells previously treated with excessive HA and in non-treated B16F1 cells by dark field bioimaging ('a' represents non-treated cells; 'b' represents cells treated with AuCM/siLuc/PEI/HA composite in a medium having no extra HA; 'c' represents cells treated with extra HA and AuCM/siLuc/PEI/HA composite together; 'd' is enlarged view of 'b').

As shown in FIG. 13, it can be seen that cellular uptake of the AuCM/siLuc/PEI/HA composite remarkably decreases when the medium contains extra HA (FIG. 13c). Thus, it can be seen that target directed cellular uptake of the AuCM/siLuc/PEI/HA composite prepared in <Example 1> is intermediated by HA receptor.

EXPERIMENTAL EXAMPLE 7

Evaluation of Target Directed Gene Silencing Activity of AuCM/siRNA/PEI/HA Composite To evaluate target directivity of the AuCM/siLuc/PEI/HA composite prepared in <Example 1>, HA receptor was blocked with free HA, and then, gene expression inhibition efficiency of the AuCM/siLuc/PEI/HA composite was evaluated.

Specifically, B16F1 cells were divided into 24 well plate at 2×10⁴ per well. After 24 hours, jetPEI/PGL3-Luc composite (jetPEI™, Polyplus-transfection Co., New York, N.Y.) was introduced at PGL3-Luc concentration of 200 nM, and the cells were cultured for 3 hours to 12 hours at 37° C. and 5% $CO_2$, and washed with PBS, and then, treated with each AuCM/siLuc, AuCM/siLuc/PEI, AuCM/siLuc/PEI/HA composite in DMEM medium containing 50% fetal bovine serum and 100 U/mL penicillin-streptomycin with/without HA (2 mg/mL). After culturing for 24 hours, Luciferase activity was measured for 30 seconds using Luminometer (Luminoskan Ascent, Lab systems, Germany), and the results are shown in FIG. 14.

Figure 14:
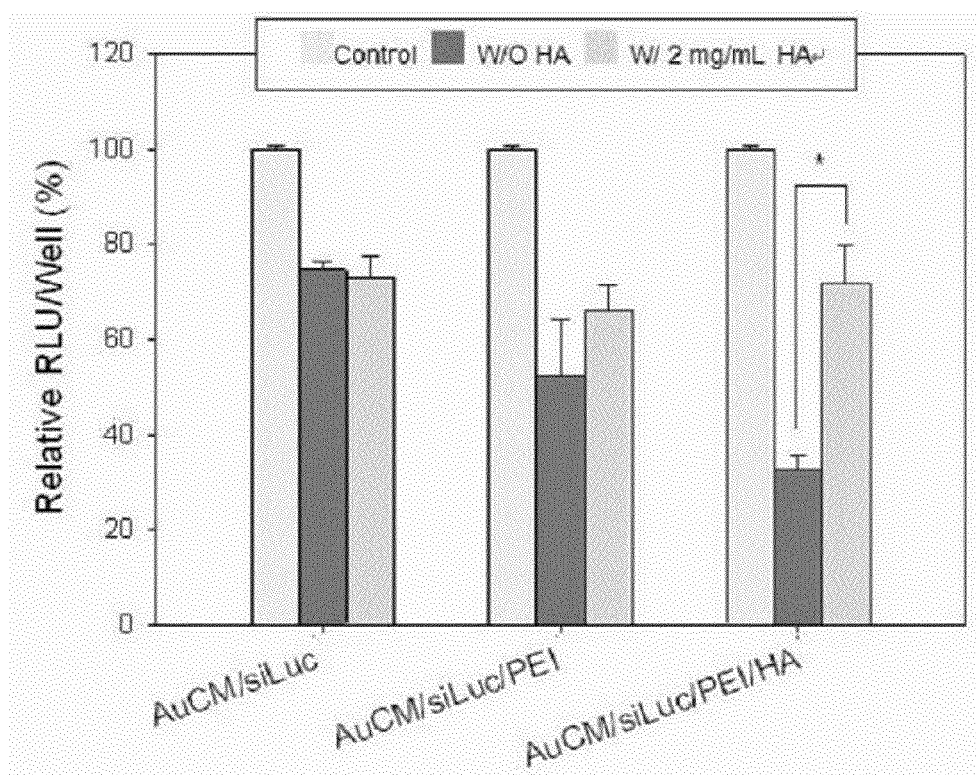
FIG. 14 shows the'results of observing the effect of inhibiting Luciferase protein of the AuCM/siLuc/PEI/HA composite in B16F1 cells previously treated with excessive HA and in non-treated B16F1 cells according to <Experimental Example 7>.

As shown in FIG. 14, although gene expression inhibition efficiencies of the AuCM/siLuc, AuCM/siLuc/PEI composites were not influenced by the addition of extra HA, gene expression inhibition efficiency of the AuCM/siLuc/PEI/HA composite rapidly decreased when extra HA existed. Thus, it was confirmed that HA coated in the outermost layer of the composite may deliver nucleic acid in the cell having HA receptor in a target directed manner, and the composite manifests target directed gene expression inhibition effect through target directed cellular uptake mediated by HA receptor, as shown in Experimental Example 6.

Experimental Example 8

Liver Tissue Gene Silencing Activity by Systemic Delivery of AuCM/siRNA/PEI/HA Composite Since HA is known to be well delivered to liver tissue having HA receptor, gene expression inhibition by systemic delivery of the AuCM/siRNA/PEI/HA composite prepared in <Example 1> was evaluated in the liver.

To inhibit gene expression of apolipoprotein B (ApoB) that is expressed much in the liver, the AuCM/siApoB/PEI/HA composite prepared according to <Example 1> using apolipoprotein B siRNA (siApoB) (SEQ ID NOs. 5 and 6) was injected into tail vein of Balb/c mice (male, 5 week old) respectively at 0.45 nmol/mouse (AuCM/siApoB/PEI/HA 1), 0.90 nmol/mouse (AuCM/siApoB/PEI/HA 2) and 1.8 nmol/mouse (AuCM/siApoB/PEI/HA 3). After 24 hours, RNA was extracted from the liver cells. 1 μg of the extracted RNA was reverse-transcribed to synthesize cDNA, and ApoB mRNA level was normalized to GAPDH mRNA level using RT-PCR and shown in FIG. 15.

Figure 15:
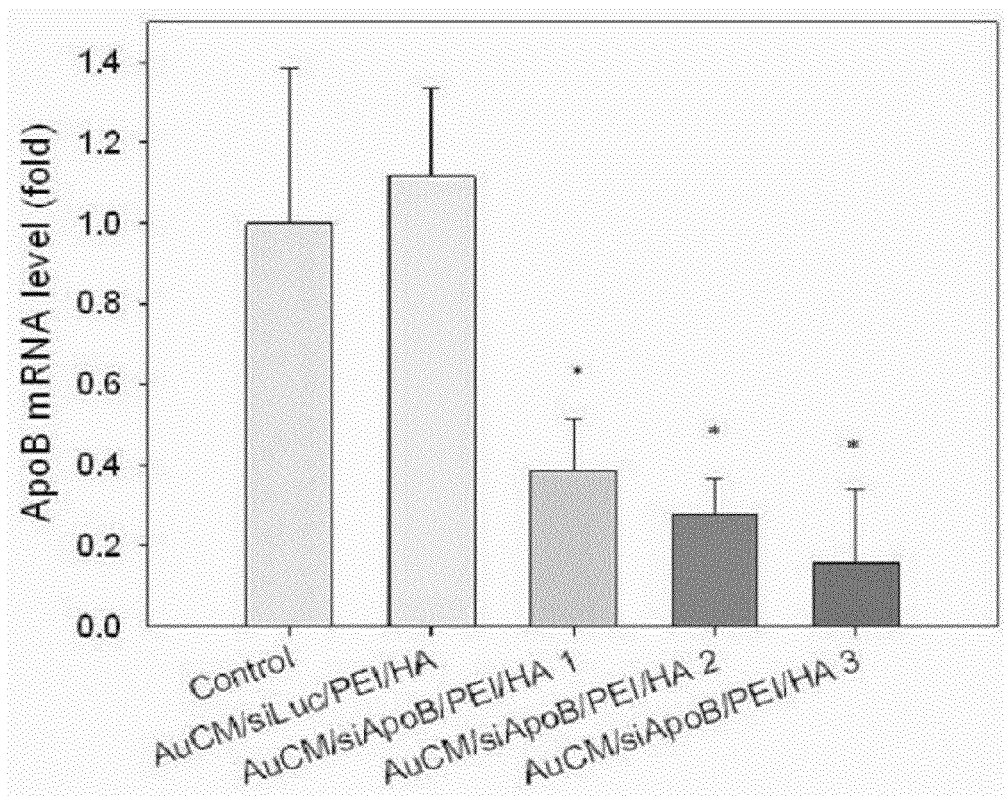
FIG. 15 shows the results of observing the effect of inhibiting APOB mRNA in the liver, after injecting the AuCM/siApoB/PEI/HA composite in Balb/c mice tail vein at various concentrations, according to <Experimental Example 8>.

1 μg of the extracted RNA was reverse-transcribed using a first strand cDNA synthesis kit according to the manufacturer's instructions to synthesize cDNA, and RT-PCR was conducted using Taq DNA polymerase by the same method as Experimental Example 5 to normalize ApoB mRNA level in the liver to GAPDH mRNA level, which is shown in FIG. 15. The sequence of the used primer is as follows (primer sequence of GAPDH is the same as Experimental Example 5).

```
<ApoB primer>
Forward direction:
                                  (SEQ ID NO.: 11)
5'-TTTTCCTCCCAGATTTCAAGG-3'

Reverse direction:
                                  (SEQ ID NO.: 12)
5'-TCCAGCATTGGTATTCAGTGTG-3'
```

As shown in FIG. 15, the AuCM/siRNA/PEI/HA composite decreased ApoB mRNA level in the liver about 60-80%, and the decrease effect is higher as the concentration of the AuCM/siRNA/PEI/HA composite increases. Specifically, AuCM/siApoB/PEI/HA 1 wherein AuCM/siApoB/PEI/HA composite is injected in Balb/c mice (male, 5 week old) in the concentration of 0.45 nmol/mouse exhibited about 40% ApoB mRNA level in the liver, while AuCM/siApoB/PEI/HA 3 of the highest concentration of 1.8 nmol/mouse exhibited about 20% ApoB mRNA level, and thus, it can be seen that ApoB mRNA level decrease effect in the liver is manifested in a concentration dependent manner.

EXPERIMENTAL EXAMPLE 9

In Vivo Distribution of AuCM/siRNA/PEI/HA Composite by Systemic Delivery

After systemic delivery of the AuCM/siRNA/PEI/HA composite prepared in <Example 1>, in vivo distribution degree of gold nanoparticles was confirmed.

Specifically, the AuCM/siLuc/PEI/HA composite prepared according to <example 1> using siLuc (SEQ ID NOs. 1 and 2) was dispersed in PBS 200 μl and systemically delivered to Balb/c mice (male, 5 week age) in the concentration of 1.8 nmol/mouse. After 24 hours, each organ was harvested and dissolved in 20 mL of aqua regia, and then, boiled until tissues are completely dissolved. After completely evaporating aqua regia, it was dissolved in 10 mL of a solution containing 1:1 of 50% nitric acid and 50% hydrochloric acid again, and diluted with distilled water. It was analyzed by ICP-AES, $Au^{3+}$ concentrations were measured according to tissues, and distribution of the prepared gold nanoparticle composite according to the organ was shown in FIG. 16.

Figure 16:
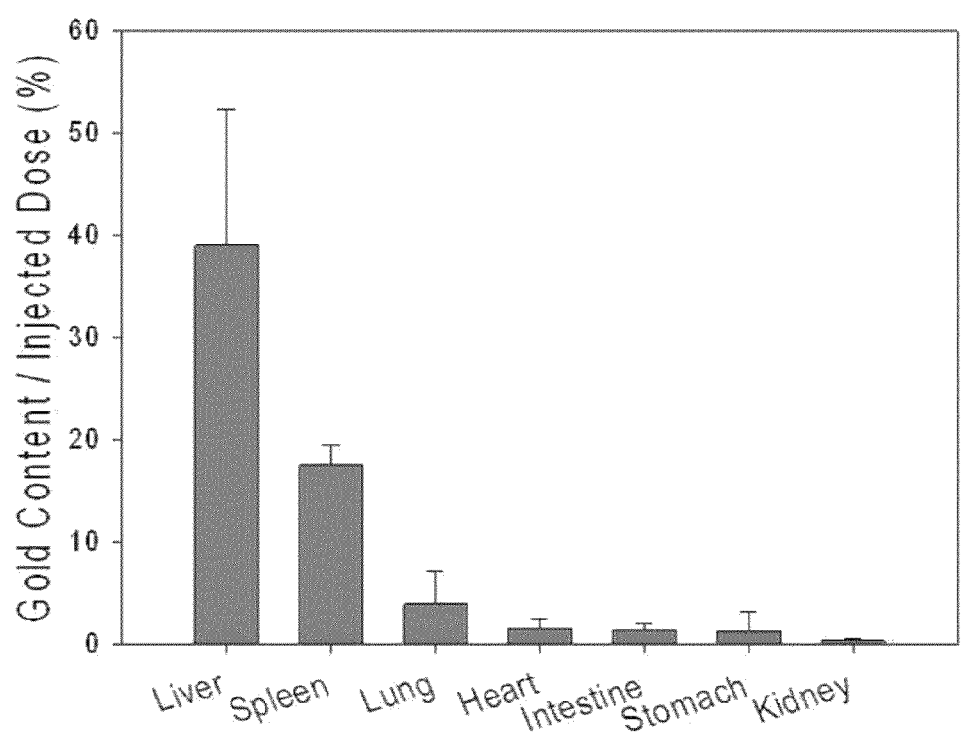
FIG. 16 shows the results of measuring distribution degree of gold in the body by ICP-AES, after injecting the AuCM/siLuc/PEI/HA composite in Balb/c mice tail vein according to <Experimental Example 9>.

As shown in FIG. 16, more than half of the injected gold nanoparticles are distributed in the liver and spleen, and particularly distributed in the liver most (about 40%). HA receptors such as HARE, CD44, LYVE-1 exist in the liver, spleen, lymph node and kidney, and the like (Kim et al., ACS Nano 4 (2010) 3005-3014), and HA was deposited in the outermost layer in the AuCM/siRNA/PEI/HA composite prepared in <Example 1>, and thus, the AuCM/siRNA/PEI/HA composite was effectively delivered to the liver through systemic delivery, and thereby, excellent gene expression inhibition effect was manifested in the liver, as confirmed in <Experimental Example 8>.

What is claimed is:

1. A composition for nucleic acid delivery comprising positively charged metal nanoparticles(s); and
a nucleic acid layer, a cationic polymer layer and an anionic polymer layer formed by coating of nucleic acid, cationic polymer and anionic polymer on the surface of the metal nanoparticle(s) by electrostatic layer by layer self assembly,
wherein the composition for nucleic acid delivery comprises 90 to 110 parts by weight of the metal nanoparticles, 3.28 to 3.93 parts by weight of the nucleic acid, 3.24 to 3.89 parts by weight of the cationic polymer, and 50.45 to 61.66 parts by weight of the anionic polymer.

2. The composition for nucleic acid delivery according to claim 1, wherein the metal nanoparticle is gold nanoparticle, silver nanoparticle, or magnetic nanoparticle having positive charge introduced on the surface.

3. The composition for nucleic acid delivery according to claim 1, wherein the metal nanoparticle includes positive charge introducing material selected from the group consisting of dopamine, polyethyleneglycol (PEG), and cysteine, bound to the surface.

4. The composition for nucleic acid delivery according to claim 1, wherein the metal nanoparticle includes cysteine bound to the surface.

5. The composition for nucleic acid delivery according to claim 1, wherein the nucleic acid is small interfering ribonucleic acid (siRNA), antisense nucleic acid, or nucleic acid aptamer.

6. The composition for nucleic acid delivery according to claim 1, wherein the nucleic acid is small interfering ribonucleic acid (siRNA), antisense nucleic acid, or nucleic acid aptamer, consisting of 5 to 200 base pairs.

7. The composition for nucleic acid delivery according to claim 1, wherein the nucleic acid is included in the mole ratio of 40 to 48:1 (nucleic acid: metal nanoparticles) to the metal nanoparticles.

8. The composition for nucleic acid delivery according to claim 1, wherein the cationic polymer is polyethyleneimine, chitosan, or polyamidoamine.

9. The composition for nucleic acid delivery according to claim 1, wherein the cationic polymer is polyethyleneimine with a molecular weight of 10 kDa to 25 kDa.

10. The composition for nucleic acid delivery according to claim 1, wherein the anionic polymer is selected from the group consisting of hyaluronic acid, dextran sulfate, heparin, heparan sulfate, chondroitin, chondroitin sulfate, keratan sulfate, dermatan sulfate, and a pharmaceutically acceptable salt thereof.

11. The composition for nucleic acid delivery according to claim 1, wherein the anionic polymer is hyaluronic acid with a molecular weight of 10 kD to 100 kD, or a pharmaceutically acceptable salt thereof.

12. A method for preparing the composition for nucleic acid delivery according to claim 1, comprising:
reacting metal nanoparticle(s) with positive charge introducing material to introduce positive charge on the surface of the metal nanoparticle(s);
coating nucleic acid on the surface of the positive charge introduced metal nanoparticle surface to form a metal nanoparticle/nucleic acid composite;
coating cationic polymer on the metal nanoparticle/nucleic acid composite to form a metal nanoparticle/nucleic acid/cationic polymer composite; and
coating anionic polymer on the metal nanoparticle/nucleic acid/cationic polymer composite to form a metal nanoparticle/nucleic acid/cationic polymer/anionic polymer composite,
wherein the nucleic acid, cationic polymer, and anionic polymer is coated by electrostatic layer by layer self assembly.

13. The method for preparing a composition for nucleic acid delivery according to claim 12, wherein the metal nanoparticle is gold nanoparticle, silver nanoparticle, or magnetic nanoparticle.

14. The method for preparing a composition for nucleic acid delivery according to claim 12, wherein the positive charge introducing material is dopamine, polyethyleneglycol (PEG), or cysteine.

15. The method for preparing a composition for nucleic acid delivery according to claim 12, wherein the step of forming the metal nanoparticle/nucleic acid composite comprises adding a solution including the metal nanoparticles to a solution including the nucleic acid.

16. The method for preparing a composition for nucleic acid delivery according to claim 15, wherein the metal nanoparticles are added such that a mole ratio of the nucleic acid coated on the metal nanoparticles and the metal nanoparticles becomes 40 to 48:1 (nucleic acid:metal nanoparticles).

17. The method for preparing a composition for nucleic acid delivery according to claim 12, wherein the nucleic acid is small interfering ribonucleic acid (siRNA), antisense nucleic acid, or nucleic acid aptamer.

18. The method for preparing a composition for nucleic acid delivery according to claim 12, wherein the cationic polymer is coated at N/P ratio of 1 to 5 to the metal nanoparticle/nucleic acid composite.

19. The method for preparing a composition for nucleic acid delivery according to claim 12, wherein the cationic polymer is polyethyleneimine, chitosan, or polyamidoamine.

20. The method for preparing a composition for nucleic acid delivery according to claim 12, wherein the anionic polymer is selected from the group consisting of hyaluronic acid, dextran sulfate, heparin, heparan sulfate, chondroitin, chondroitin sulfate, keratan sulfate, dermatan sulfate, and a pharmaceutically acceptable salt thereof.

* * * * *